United States Patent
Laurent et al.

(10) Patent No.: US 9,447,102 B2
(45) Date of Patent: Sep. 20, 2016

(54) PROTEIN KINASE INHIBITORS

(71) Applicant: Pharmascience, Inc., Montreal (CA)

(72) Inventors: Alain Laurent, Montreal (CA); Yannick Rose, Montreal (CA)

(73) Assignee: PHARMASCIENCE, INC. (CA)

( * ) Notice: Subject to any disclaimer, the term of this patent is extended or adjusted under 35 U.S.C. 154(b) by 0 days.

(21) Appl. No.: 14/412,982

(22) PCT Filed: Jul. 3, 2013

(86) PCT No.: PCT/CA2013/000612
§ 371 (c)(1),
(2) Date: Jan. 5, 2015

(87) PCT Pub. No.: WO2014/005217
PCT Pub. Date: Jan. 9, 2014

(65) Prior Publication Data
US 2015/0344478 A1  Dec. 3, 2015

(30) Foreign Application Priority Data
Jul. 6, 2012 (CA) .................................... 2782774

(51) Int. Cl.
C07D 487/04 (2006.01)
A61K 31/4162 (2006.01)
(52) U.S. Cl.
CPC ......... C07D 487/04 (2013.01); A61K 31/4162 (2013.01)
(58) Field of Classification Search
CPC .................. C07D 487/04; A61K 31/4162
USPC ........................... 544/262; 514/262.1
See application file for complete search history.

(56) References Cited

FOREIGN PATENT DOCUMENTS

CA  2385769 A1  3/2001

OTHER PUBLICATIONS

GVK BIO Database RN 1347966-28-2, Dec. 2011.*
Ten Hacken et al., Microenvironment dependency in Chronic Lymphocytic Leukemia: The basis for new targeted therapies, 11 pages, Pharmacology & Therapeutics, (2014), http://dx.doi.org/10.1016/j.pharmthera.2014.07.003.*
Gura et al., Systems for identifying new drugs are often faulty, Science, 278:1041-1042, 1997.*
Johnson et al., Relationships between drug activity in NCI preclinical in vitro and in vivo models and early clinical trials, British Journal of Cancer, 84(10):1424-1431,2001.*
Pearce et al., Failure modes in anticancer drug discovery and development, Cancer Drug Design and Discovery Edited by Stephen Neidle, Chapter 18, pp. 424-435 (2008).*
Simone, Oncology: Introduction, Cecil Textbook of Medicine, 20th Edition, vol. 1, pp. 1004-101 O, 1995.*

* cited by examiner

*Primary Examiner* — Deepak Rao
(74) *Attorney, Agent, or Firm* — Troutman Sanders LLP

(57) ABSTRACT

The present invention relates to a novel family of inhibitors of protein kinase of formula 1 and process for their production and pharmaceutical compositions thereof. In particular, the present invention relates to inhibitors of the members of the Tec, Src and Btk protein kinase families.

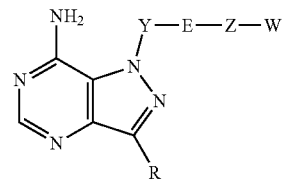

Formula 1

7 Claims, No Drawings

PROTEIN KINASE INHIBITORS

CROSS REFERENCE TO RELATED APPLICATIONS

The present application claims the benefit of priority to PCT International Application No. PCT/CA13/00612 filed 3 Jul. 2013, which claims the benefit of priority to CA Application No. 2,782,774 filed 6 Jul. 2012; each of which is incorporated herein by reference in its entirety.

FIELD OF INVENTION

The present invention relates to a novel family of inhibitors of protein kinases. In particular, the present invention relates to inhibitors of the members of the Tec and Src protein kinase families, more particularly Btk.

BACKGROUND OF THE INVENTION

Protein kinases are a large group of intracellular and transmembrane signaling proteins in eukaryotic cells. These enzymes are responsible for transfer of the terminal (gamma) phosphate from ATP to specific amino acid residues of target proteins. Phosphorylation of specific tyrosine, serine or threonine amino acid residues in target proteins can modulate their activity leading to profound changes in cellular signaling and metabolism. Protein kinases can be found in the cell membrane, cytosol and organelles such as the nucleus and are responsible for mediating multiple cellular functions including metabolism, cellular growth and division, cellular signaling, modulation of immune responses, and apoptosis. The receptor tyrosine kinases are a large family of cell surface receptors with protein tyrosine kinase activity that respond to extracellular cues and activate intracellular signaling cascades (Plowman et al. (1994) DN&P, 7(6):334-339).

Aberrant activation or excessive expression of various protein kinases are implicated in the mechanism of multiple diseases and disorders characterized by benign and malignant proliferation, excess angiogenesis, as well as diseases resulting from inappropriate activation of the immune system. Thus, inhibitors of select kinases or kinase families are expected to be useful in the treatment of cancer, autoimmune diseases, and inflammatory conditions including, but not limited to: solid tumors, hematological malignancies, arthritis, graft versus host disease, lupus erythematosus, psoriasis, colitis, illeitis, multiple sclerosis, uveitis, coronary artery vasculopathy, systemic sclerosis, atherosclerosis, asthma, transplant rejection, allergy, dermatomyositis, pemphigus and the like.

Examples of kinases that can be targeted to modulate disease include receptor tyrosine kinases such as members of the platelet-derived growth factor receptor (PDGFR), vascular endothelial growth factor receptor (VEGFR) families and intracellular proteins such as members of the Syk, SRC, and Tec families of kinases.

Tec kinases are non-receptor tyrosine kinases predominantly, but not exclusively, expressed in cells of hematopoietic origin (Bradshaw J M. Cell Signal. 2010, 22:1175-84). The Tec family includes Tec, Bruton's tyrosine kinase (Btk), inducible T-cell kinase (Itk), resting lymphocyte kinase (Rlk/Txk), and bone marrow-expressed kinase (Bmx/Etk). Btk is a Tec family kinase which is important in B-cell receptor signaling. Btk is activated by Src-family kinases and phosphorylates PLC gamma leading to effects on B-cell function and survival. Additionally, Btk is important in signal transduction in response to immune complex recognition by macrophage, mast cells and neutrophils. Btk inhibition is also important in survival of lymphoma cells (Herman, SEM. Blood 2011, 117:6287-6289) suggesting that inhibition of Btk may be useful in the treatment of lymphomas. As such, inhibitors of Btk and related kinases are of great interest as anti-inflammatory as well as anticancer agents.

cSRC is the prototypical member of the SRC family of tyrosine kinases which includes Lyn, Fyn, Lck, Hck, Fgr, Blk, Syk, Yrk, and Yes. cSRC is critically involved in signaling pathways involved in cancer and is often overexpressed in human malignancies (Kim L C, Song L, Haura E B. Nat Rev Clin Oncol. 2009 6(10):587-9). The role of cSRC in cell adhesion, migration and bone remodeling strongly implicate this kinase in the development and progression of bone metastases. cSRC is also involved in signaling downstream of growth factor receptor tyrosine kinases and regulates cell cycle progression suggesting that cSRC inhibition would impact cancer cell proliferation. Additionally, inhibition of SRC family members may be useful in treatments designed to modulate immune function. SRC family members, including Lck, regulate T-cell receptor signal transduction which leads to gene regulation events resulting in cytokine release, survival and proliferation. Thus, inhibitors of Lck have been keenly sought as immunosuppressive agents with potential application in graft rejection and T-cell mediated autoimmune disease (Martin et al. Expert Opin Ther Pat. 2010, 20:1573-93).

Inhibition of kinases using small molecule inhibitors has successfully led to several approved therapeutic agents used in the treatment of human conditions. Herein, we disclose a novel family of kinase inhibitors. Further, we demonstrate that modifications in compound substitution can influence kinase selectivity and therefore the biological function of that agent.

SUMMARY OF THE INVENTION

The present invention relates to a novel family of kinase inhibitors. Compounds of this class have been found to have inhibitory activity against members of the Tec and Src protein kinase families, more particularly Btk.

One aspect of the present invention is directed to a compound of Formula 1:

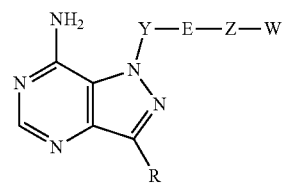

Formula 1 wherein
R is selected from the group consisting of:
1) hydrogen,
2) alkyl,
3) heteroalkyl,
4) carbocyclyl,
5) heterocyclyl;
   wherein the alkyl, heteroalkyl, carbocyclyl and heterocyclyl may be further substituted.

Y is

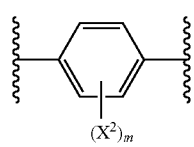

E is selected from oxygen,
Z is selected from:

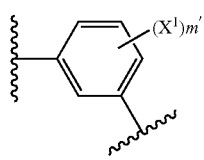

Wherein Y-E-Z—W is

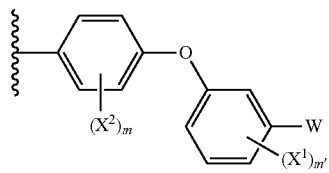

$X^1$ and $X^2$ are independently selected from hydrogen and halogen;
n is an integer from 0 to 2;
m is an integer from 0 to 2;
m' is an integer from 0 to 2;
  W is independently selected from:
  1) alkyl,
  2) aralkyl,
  3) heteroaralkyl,
  4) —$OR^3$,
  5) —$OC(O)R^4$,
  6) —$OC(O)NR^5R^6$,
  7) —$CH_2O$—$R^4$,
  8) —$NR^5R^6$,
  9) —$NR^2C(O)R^4$
  10) —$NR^2S(O)_nR^4$,
  11) —$NR^2C(O)NR^5R^6$;
wherein the alkyl, aralkyl and heteroaralkyl may be further substituted;
$R^2$ is selected from hydrogen or alkyl;
$R^3$ is selected from substituted or unsubstituted alkyl, alkenyl, alkynyl, heteroalkyl, carbocyclyl, heterocyclyl, aryl, heteroaryl, aralkyl or heteroaralkyl;
$R^4$ is selected from substituted or unsubstituted alkyl, alkenyl, alkynyl, heteroalkyl, carbocyclyl, heterocyclyl, aryl or heteroaryl; and
$R^5$ and $R^6$ are independently selected from hydrogen, alkyl, alkenyl, alkynyl, heteroalkyl, carbocyclyl, heterocyclyl, aryl, heteroaryl or $R^5$ and $R^6$ can be fused to form a 3 to 8 membered heterocyclyl ring system.
  Preferred embodiments include compounds of Formula 1 where W is selected from —$OR^3$ and $R^3$ is selected from substituted or unsubstituted aralkyl, or substituted or unsubstituted heteroaralkyl.
  More preferred embodiments include compounds of Formula 1 where W is selected from the group consisting of:

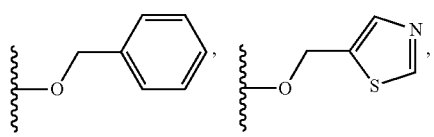

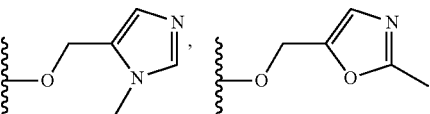

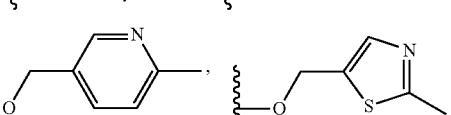

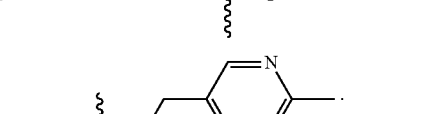

Even more preferred embodiments include compounds of Formula 1 where Y is selected from the group consisting of:

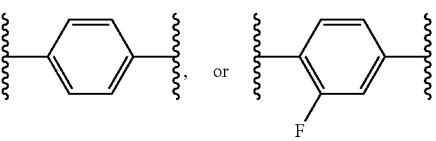

Preferred embodiments include compounds of Formula 1 where Z is selected from the group consisting of:

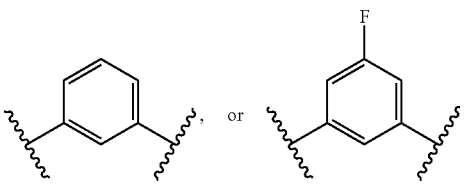

Preferred embodiment includes compounds of Formula 1 where R is selected from the group consisting of:

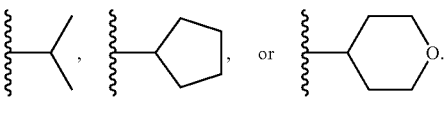

More preferred embodiments include compounds of Formula 1 where W is selected from the group consisting of:

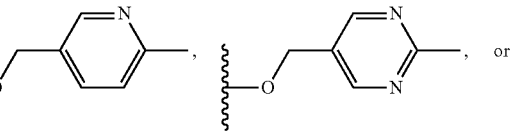

-continued

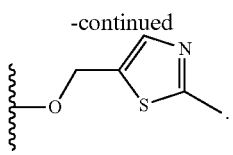

More preferred embodiments include compounds of Formula 1 where Z is selected from the group consisting of:

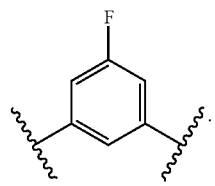 [SMILES: *c1cc(*)cc(F)c1]

Another aspect of the present invention provides a pharmaceutical composition comprising an effective amount of a compound of Formula 1 and a pharmaceutically acceptable carrier, diluent or excipient.

In another aspect of the present invention, there is provided a use of the compound of Formula 1 as an inhibitor of protein kinase, more particularly, as an inhibitor of Btk.

Another aspect of the present invention provides a method of modulating kinase function, the method comprising contacting a cell with a compound of the present invention in an amount sufficient to modulate the enzymatic activity of a given kinase or kinases, such as Btk, thereby modulating the kinase function.

Another aspect of the present invention provides a method of modulating the target kinase function, the method comprising a) contacting a cell with a compound of the present invention in an amount sufficient to modulate the target kinase function, thereby b) modulating the target kinase activity and signaling.

Another aspect of the present invention provides a probe, the probe comprising a compound of Formula 1 labeled with a detectable label or an affinity tag. In other words, the probe comprises a residue of a compound of Formula 1 covalently conjugated to a detectable label. Such detectable labels include, but are not limited to, a fluorescent moiety, a chemiluminescent moiety, a paramagnetic contrast agent, a metal chelate, a radioactive isotope-containing moiety, or biotin.

DETAILED DESCRIPTION OF PREFERRED EMBODIMENTS

The present invention relates to novel kinase inhibitors. These compounds are found to have activity as inhibitors of protein kinases, including members of the tyrosine kinases Aurora, SRC (more specifically Lck) and Tec (more specifically Btk) kinase families.

Compounds of the present invention may be formulated into a pharmaceutical composition which comprises an effective amount of a compound of Formula 1 with a pharmaceutically acceptable diluent or carrier. For example, the pharmaceutical compositions may be in a conventional pharmaceutical form suitable for oral administration (e.g., tablets, capsules, granules, powders and syrups), parenteral administration (e.g., injections (intravenous, intramuscular, or subcutaneous)), drop infusion preparations, inhalation, eye lotion, topical administration (e.g., ointment), or suppositories. Regardless of the route of administration selected, the compounds may be formulated into pharmaceutically acceptable dosage forms by conventional methods known to those skilled in the art.

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition, or vehicle, such as a liquid or solid filler, diluent, excipient, solvent or encapsulating material. Each carrier must be acceptable in the sense of being compatible with the other ingredients of the formulation, including the active ingredient, and not injurious or harmful to the patient. Some examples of materials which can serve as pharmaceutically acceptable carriers include: (1) sugars, such as lactose, glucose, and sucrose; (2) starches, such as corn starch, potato starch, and substituted or unsubstituted β-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically acceptable salt" refers to the relatively non-toxic, inorganic and organic acid addition salts of the compound(s). These salts can be prepared in situ during the final isolation and purification of the compound(s), or by separately reacting a purified compound(s) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like (See, for example, Berge et al. (1977) "Pharmaceutical Salts", *J. Pharm. Sci.* 66: 1-19).

In other cases, the compounds of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of a compound(s). These salts can likewise be prepared in situ during the final isolation and purification of the compound(s), or by separately reacting the purified compound(s) in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

As used herein, the term "affinity tag" means a ligand or group, linked either to a compound of the present invention or to a protein kinase domain, that allows the conjugate to be extracted from a solution.

The term "alkyl" refers to substituted or unsubstituted saturated hydrocarbon groups, including straight-chain alkyl and branched-chain alkyl groups, including haloalkyl groups such as trifluoromethyl and 2,2,2-trifluoroethyl, etc. Representative alkyl groups include methyl, ethyl, n-propyl, isopropyl, n-butyl, t-butyl, isobutyl, sec-butyl, (cyclohexyl) methyl, cyclopropylmethyl, n-pentyl, n-hexyl, n-heptyl, n-octyl, and the like. The terms "alkenyl" and "alkynyl" refer to substituted or unsubstituted unsaturated aliphatic groups analogous in length and possible substitution to the alkyls described above, but that contain at least one double or triple bond respectively. Representative alkenyl groups include vinyl, propen-2-yl, crotyl, isopenten-2-yl, 1,3-butadien-2-yl), 2,4-pentadienyl, and 1,4-pentadien-3-yl. Representative alkynyl groups include ethynyl, 1- and 3-propynyl, and 3-butynyl. In certain preferred embodiments, alkyl substituents are lower alkyl groups, e.g., having from 1 to 6 carbon atoms. Similarly, alkenyl and alkynyl preferably refer to lower alkenyl and alkynyl groups, e.g., having from 2 to 6 carbon atoms. As used herein, "alkylene" refers to an alkyl group with two open valencies (rather than a single valency), such as $-(CH_2)_{1-10}-$ and substituted variants thereof.

The term "alkoxy" refers to an alkyl group having an oxygen attached thereto. Representative alkoxy groups include methoxy, ethoxy, propoxy, tert-butoxy and the like. An "ether" is two hydrocarbons covalently linked by an oxygen. Accordingly, the substituent of an alkyl that renders that alkyl an ether is or resembles an alkoxy.

The term "alkoxyalkyl" refers to an alkyl group substituted with an alkoxy group, thereby forming an ether.

The terms "amide" and "amido" are art-recognized as an amino-substituted carbonyl and includes a moiety that can be represented by the general formula:

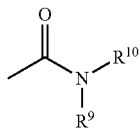

wherein $R^9$, $R^{10}$ are as defined above. Preferred embodiments of the amide will not include imides, which may be unstable.

The terms "amine" and "amino" are art-recognized and refer to both unsubstituted and substituted amines and salts thereof, e.g., a moiety that can be represented by the general formulae:

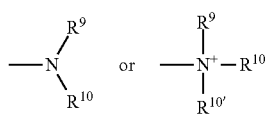

wherein $R^9$, $R^{10}$ and $R^{10'}$ each independently represent a hydrogen, an alkyl, an alkenyl, $-(CH_2)_p-R^8$, or $R^9$ and $R^{10}$ taken together with the N atom to which they are attached complete a heterocycle having from 4 to 8 atoms in the ring structure; $R^8$ represents an aryl, a cycloalkyl, a cycloalkenyl, a heterocyclyl or a polycyclyl; and p is zero or an integer from 1 to 8. In preferred embodiments, only one of $R^9$ or $R^{10}$ can be a carbonyl, e.g., $R^9$, $R^{10}$, and the nitrogen together do not form an imide. In even more preferred embodiments, $R^9$ and $R^{10}$ (and optionally $R^{10'}$) each independently represent a hydrogen, an alkyl, an alkenyl, or $-(CH_2)_p-R^8$. In certain embodiments, the amino group is basic, meaning the protonated form has a $pK_a \geq 7.00$.

The term "aralkyl", as used herein, refers to an alkyl group substituted with an aryl group, for example $-(CH_2)_p-Ar$.

The term "heteroaralkyl", as used herein, refers to an alkyl group substituted with a heteroaryl group, for example $-(CH_2)_p-Het$.

The term "aryl" as used herein includes 5-, 6-, and 7-membered substituted or unsubstituted single-ring aromatic groups in which each atom of the ring is carbon. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, anthracene, and phenanthrene.

The terms "carbocycle" and "carbocyclyl", as used herein, refer to a non-aromatic substituted or unsubstituted ring in which each atom of the ring is carbon. The terms "carbocycle" and "carbocyclyl" also include polycyclic ring systems having two or more cyclic rings in which two or more carbons are common to two adjoining rings wherein at least one of the rings is carbocyclic, e.g., the other cyclic rings can be cycloalkyls, cycloalkenyls, cycloalkynyls, aryls, heteroaryls, and/or heterocyclyls. Representative carbocyclic groups include cyclopentyl, cyclohexyl, 1-cyclohexenyl, and 3-cyclohexen-1-yl, cycloheptyl.

The term "carbonyl" is art-recognized and includes such moieties as can be represented by the general formula:

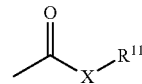

wherein X is a bond or represents an oxygen or a sulfur, and $R^{11}$ represents a hydrogen, an alkyl, an alkenyl, $-(CH_2)_p-R^8$ or a pharmaceutically acceptable salt. Where X is oxygen and $R^{11}$ is not hydrogen, the formula represents an "ester". Where X is oxygen, and $R^{11}$ is hydrogen, the formula represents a "carboxylic acid".

The terms "heteroaryl" includes substituted or unsubstituted aromatic 5- to 7-membered ring structures, more preferably 5- to 6-membered rings, whose ring structures include one to four heteroatoms. The term "heteroaryl" also includes polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, isoxazole, oxazole, thiazole, triazole, pyrazole, pyridine, pyrazine, pyridazine and pyrimidine, and the like.

The term "heteroatom" as used herein means an atom of any element other than carbon or hydrogen. Preferred heteroatoms are nitrogen, oxygen, and sulfur.

The terms "heterocyclyl" or "heterocyclic group" refer to substituted or unsubstituted non-aromatic 3- to 10-membered ring structures, more preferably 3- to 7-membered rings, whose ring structures include one to four heteroatoms. The term terms "heterocyclyl" or "heterocyclic group" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, tetrahydrofuran, tetrahydropyran, piperidine, piperazine, pyrrolidine, morpholine, lactones, and lactams.

The term "hydrocarbon", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The terms "polycyclyl" or "polycyclic" refer to two or more rings (e.g., cycloalkyls, cycloalkenyls, cycloalkynyls, aryls, heteroaryls, and/or heterocyclyls) in which two or more carbons are common to two adjoining rings, e.g., the rings are "fused rings". Each of the rings of the polycycle can be substituted or unsubstituted.

As used herein, the term "probe" means a compound of the invention which is labeled with either a detectable label or an affinity tag, and which is capable of binding, either covalently or non-covalently, to a protein kinase domain. When, for example, the probe is non-covalently bound, it may be displaced by a test compound. When, for example, the probe is bound covalently, it may be used to form cross-linked adducts, which may be quantified and inhibited by a test compound.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

Compounds of the invention also include all isotopes of atoms present in the intermediates and/or final compounds. Isotopes include those atoms having the same atomic number but different mass numbers. For example, isotopes of hydrogen include deuterium and tritium.

General Synthetic Methods

The following section describes general synthetic method(s) which may be useful in the preparation of compounds of the instant invention.

General Synthetic Method A:

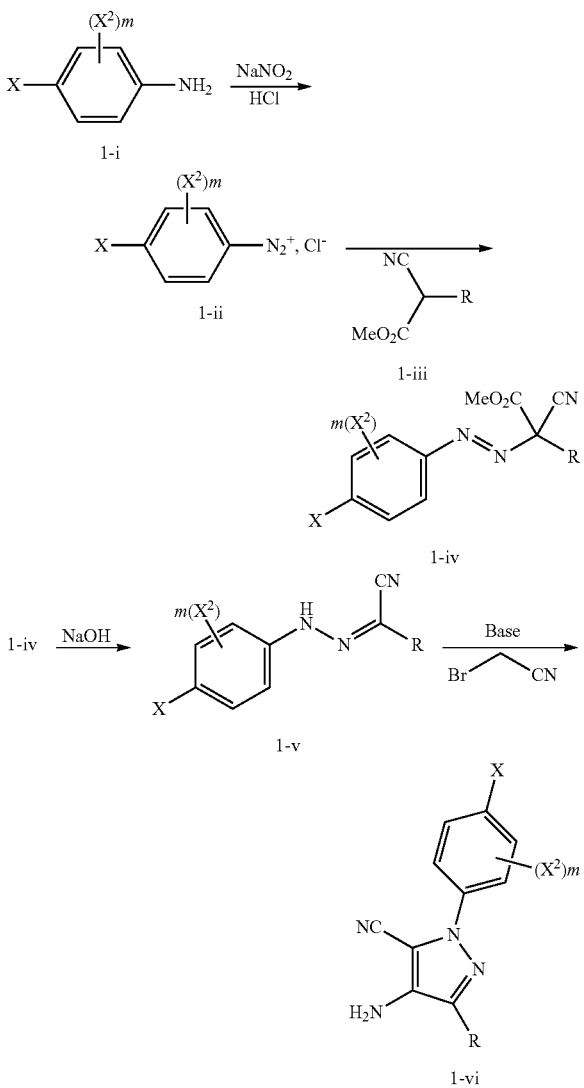

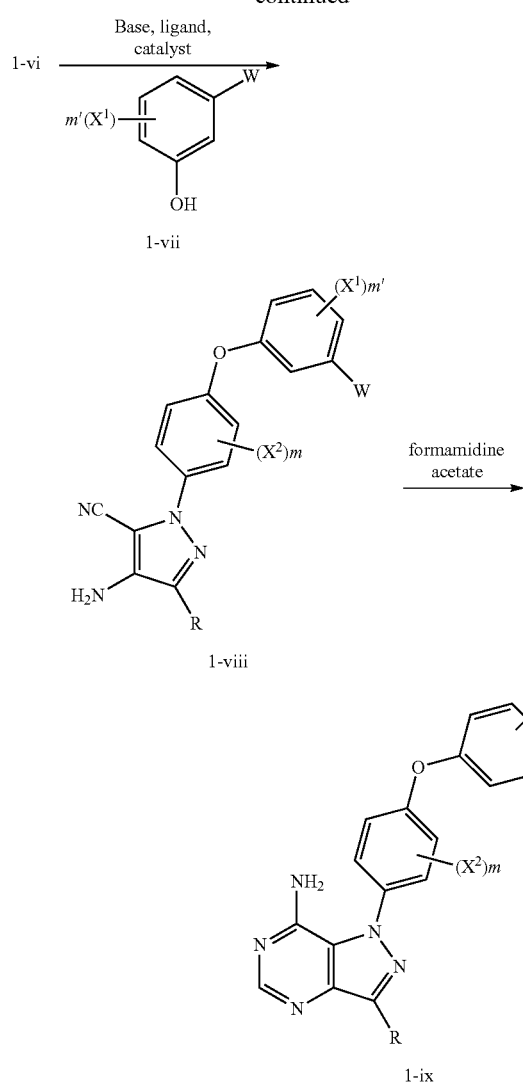
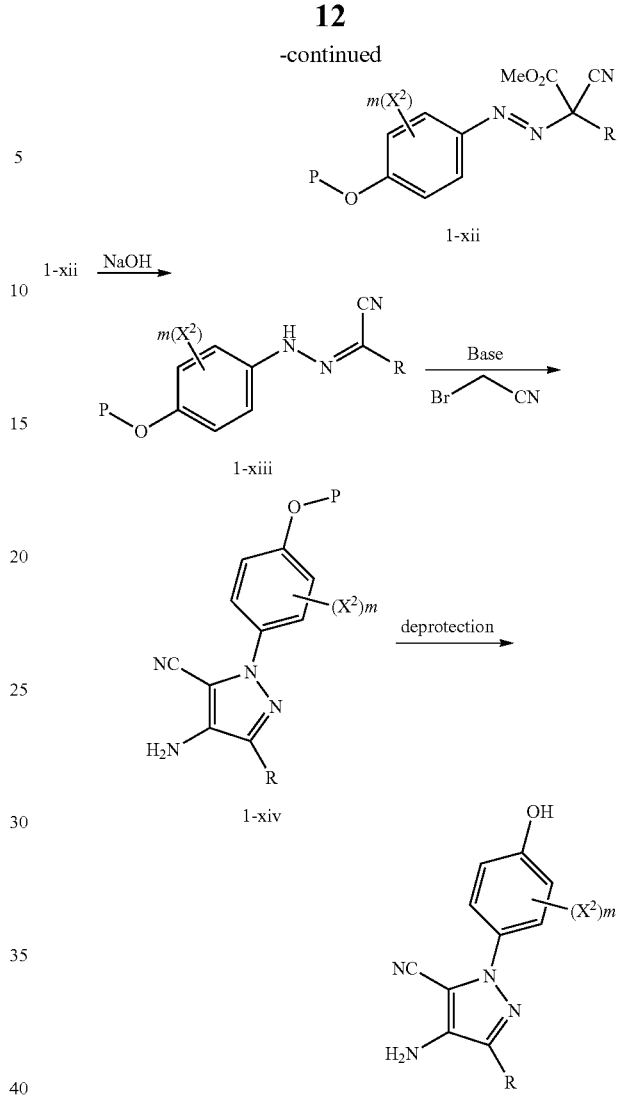
General Synthetic Method B:
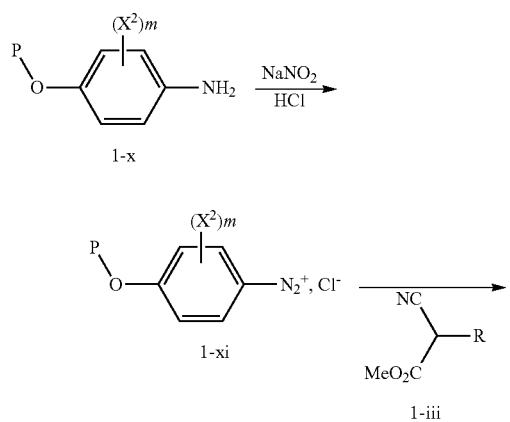
P = protective group

EXAMPLES

The following synthetic methods are intended to be representative of the chemistry used to prepare compounds of Formula 1 and are not intended to be limiting.

Synthesis of Intermediate 2-c

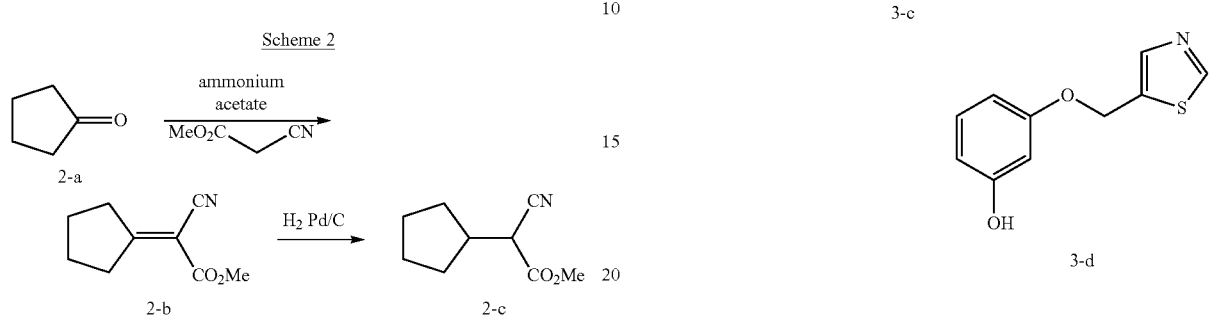

Step 1: Intermediate 2-b

To a solution of cyclopentanone (12.73 g, 151.0 mmol) in dry benzene (15.2 ml) was added methyl 2-cyanoacetate (15.0 g, 151.0 mmol), ammonium acetate (1.52 g, 19.68 mmol) and acetic acid (3.04 ml). The reaction mixture was heated to reflux in a Dean-Stark apparatus for 12 hours and then cooled to room temperature. Volatiles were removed in vacuo. Water and ethyl acetate were added to the residue, the organic layer was separated, washed with water, dried over MgSO$_4$, filtered and concentrated under reduced pressure to provide intermediate 2-b as brown oil.

Step 2: Intermediate 2-c

To a solution of intermediate 2-b (25.0 g, 151.0 mmol) in methanol, stirred under nitrogen, was added 10% Pd/C (3.22 g, 1.51 mmol). The reaction mixture was purged with H$_2$, stirred overnight under 1 atm of hydrogen and filtered through celite. The filtrate was concentrated in vacuo to provide intermediate 2-c as a yellow oil.

Synthesis of Intermediate 3-d

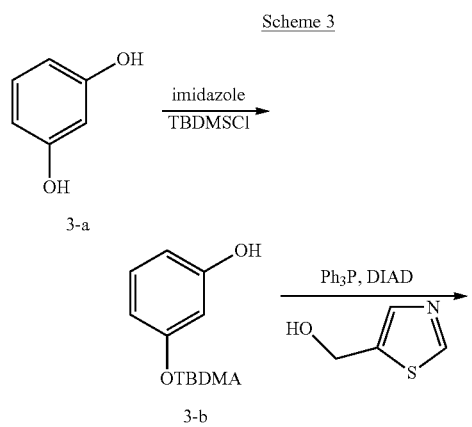

Step 1: Intermediate 3-b

To a solution of resorcinol (11.83 g, 107 mmol) in DMF (50 ml) cooled to 0° C. was added imidazole (15.36 g, 226 mmol) and tert-butylchlorodimethylsilane (17.0 g, 113 mmol). The reaction was stirred at room temperature overnight. A saturated aqueous solution of ammonium chloride and ethyl acetate were added; the organic layer was separated, washed 3 times with a saturated aqueous solution of ammonium chloride and brine, dried over MgSO$_4$, filtered and concentrated under reduced pressure. Purification by silica gel chromatography provided intermediate 3-b as a colorless oil.

Step 2: Intermediate 3-c

To a solution of intermediate 3-b (1.94 g, 8.68 mmol) and thiazol-5-ylmethanol (1.0 g, 8.68 mmol) in THF (20 ml) were sequentially added triphenylphosphine (3.42 g, 13.0 mmol) and DIAD (2.52 ml, 13.0 mmol) and the reaction was then stirred at room temperature overnight. Volatiles were removed under reduced pressure. Purification by silica gel chromatography provided intermediate 3-c as a yellow oil.

Step 3: Intermediate 3-d

To a solution of intermediate 3-c (1.6 g, 4.98 mmol) in THF (20 ml) was added a 1.0 M solution of TBAF in THF (5.47 ml, 5.47 mmol) and the reaction was stirred at room temperature for 1 hour. A saturated aqueous solution of ammonium chloride and ethyl acetate were added, the organic layer was separated, washed with brine, dried over MgSO$_4$, filtered and concentrated under reduced pressure. Diethyl ether was added to the residue; a precipitate formed and was collected by filtration to provide intermediate 3-d as a white solid.

Synthesis of Intermediate 4-d

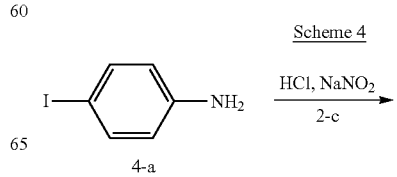

-continued

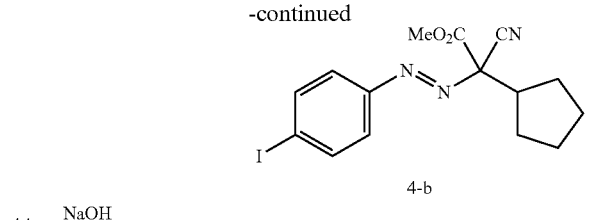

4-b 4-b $\xrightarrow{\text{NaOH}}$

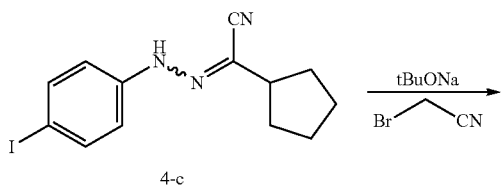

4-c

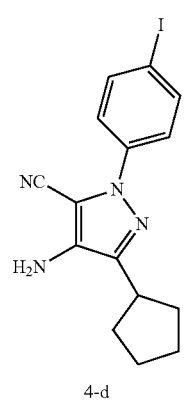

4-d

Step 1: Intermediate 4-b

To a solution of 4-iodoaniline (13.14 g, 60.0 mmol) in 1N HCl (150 ml) was added dropwise a 1.0 M aqueous solution of sodium nitrite (60.0 ml, 60.0 mmol) at room temperature, the mixture was stirred for 1 hour and then added dropwise to an ice cooled solution of intermediate 2-c (5.0 g, 29.9 mmol) in ethanol (41.7 ml) and water (556 mL). The pH was maintained at 7 by adding sodium acetate portion wise. The mixture was stirred at 0° C. for 3 hours and then room temperature until completion. A saturated aqueous solution of ammonium chloride and ethyl acetate were added, the organic layer was separated, washed with brine, dried over MgSO$_4$, filtered and concentrated under reduced pressure to provide intermediate 4-b as a beige oil.

Step 2: Intermediate 4-c

To a solution of intermediate 4-b (7.0 g, 17.6 mmol) in THF (176 ml) cooled to 0° C. was added 10N aqueous NaOH (44.1 ml, 441.0 mmol) and the reaction was stirred at room temperature overnight. A saturated aqueous solution of ammonium chloride and ethyl acetate were added, the organic layer was separated, washed with 10% citric acid, saturated aqueous NaHCO$_3$ and brine, dried over MgSO$_4$, filtered and concentrated under reduced pressure. Purification by silica gel chromatography provided intermediate 4-c as a yellow solid.

Step 3: Intermediate 4-d

To a solution of intermediate 4-c (2.1 g, 6.19 mmol) and bromoacetonitrile (474 μl, 6.81 mmol) in tert-butanol (31.0 ml) was added a 1.0 M solution of sodium tert-butoxide in tert-butanol (6.19 ml, 6.19 mmol). The reaction was then stirred at room temperature for 2 hours. A saturated aqueous solution of ammonium chloride and ethyl acetate were added, the organic layer was separated, washed with brine, dried over MgSO$_4$, filtered and concentrated under reduced pressure. Purification by silica gel chromatography provided intermediate 4-d as a yellow solid.

Synthesis of Compound 1

Scheme 5

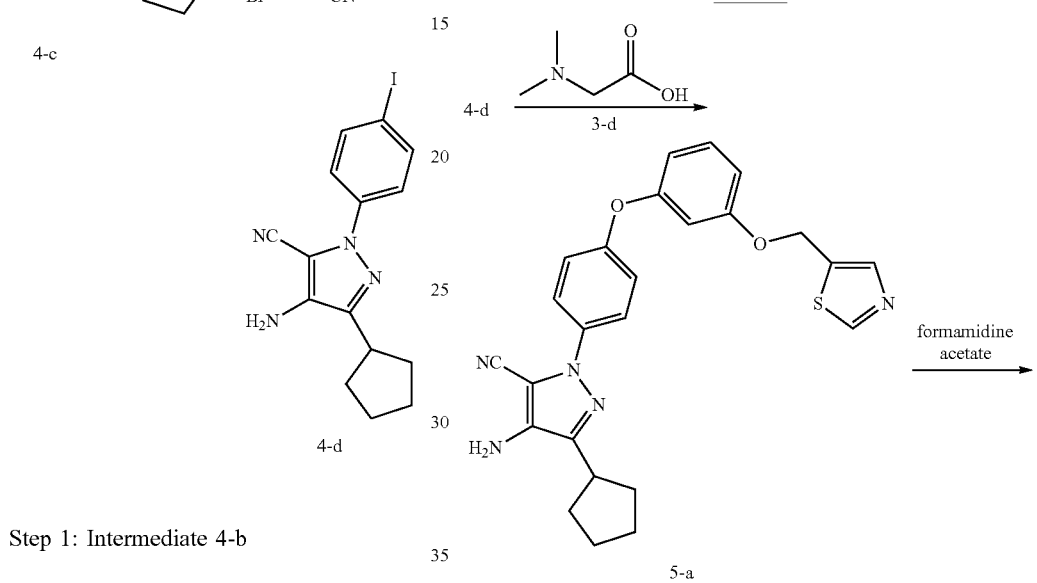

5-a

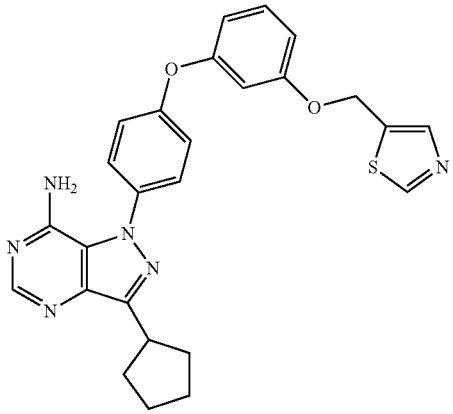

Compound 1

Step 1: Intermediate 2-1

To a solution of intermediate 3-d (125 mg, 0.60 mmol) and intermediate 4-d (200 mg, 0.60 mmol) in 1,4-dioxane were sequentially added N,N-dimethylglycine (37 mg, 0.36 mmol), cesium carbonate (393 mg, 1.20 mmol) and copper (I) iodide (23 mg, 0.12 mmol). The reaction was stirred at reflux overnight and then cooled to room temperature. Water and ethyl acetate were added, the organic layer was separated, washed with brine, dried over MgSO$_4$, filtered and concentrated under reduced pressure to provide intermediate 5-a as a brown solid.

Step 11: Compound 1

To a solution of intermediate 5-a (150 mg, 0.32 mmol) in EtOH (3.0 ml) was added formamidine acetate (265 mg, 2.54 mmol) and the reaction was stirred at 80° C. for 3 hours, then cooled to room temperature. Volatiles were removed under reduced pressure. Purification by reverse phase chromatography eluting with a 0.1% aqueous HCl/methanol gradient provided compound 1·2HCl as white solid. MS (m/z) M+H=485.2

Synthesis of Intermediate 6-c

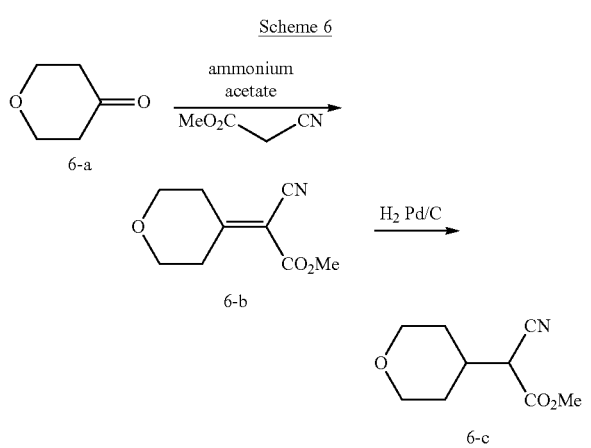

Step 1: Intermediate 6-b

To a solution of intermediate 6-a (5.05 g, 50.5 mmol) in dry benzene (5.0 ml) was added methyl 2-cyanoacetate (5.0 g, 50.5 mmol), ammonium acetate (506 mg, 6.56 mmol) and acetic acid (1.0 ml). The reaction mixture was heated to reflux, using a Dean-Stark apparatus, for 12 hours and then cooled to room temperature. Volatiles were removed in vacuo. Water and ethyl acetate were added to the residue, the organic layer was separated, washed with water, dried over MgSO$_4$, filtered and concentrated under reduced pressure to provide intermediate 6-b as a brown oil.

Step 2: Intermediate 6-c

To a solution of intermediate 6-b (9.0 g, 49.7 mmol) in methanol, under nitrogen, was added 10% Pd/C (1.06 g, 0.49 mmol). The reaction mixture was purged with H$_2$ and stirred overnight under 1 atm of hydrogen. The reaction was then filtered through celite and the filtrate was concentrated under reduced pressure to provide intermediate 6-c as a yellow oil.

Synthesis of Intermediate 7-d

Scheme 7

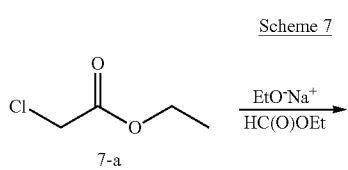

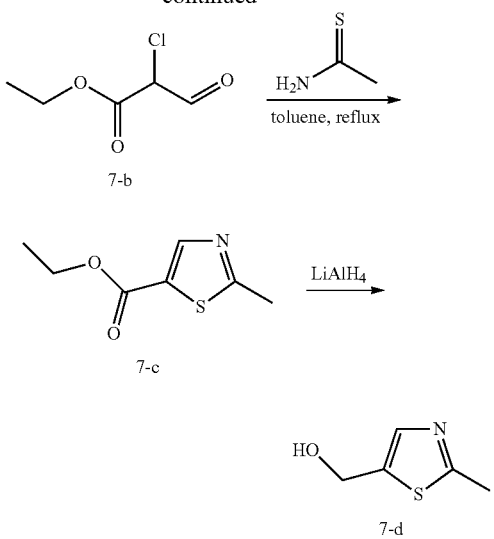

Step 1: Intermediate 7-b

Ethyl chloroacetate (50.0 g, 0.41 mol) and ethyl formate (30.2 g, 0.41 mol) were dissolved in anhydrous toluene (500 mL) and cooled to 0° C. Sodium ethoxide (35.1 g, 0.49 mol) was added portion wise. The reaction mixture was stirred at 0° C. for 5 hours and then at room temperature overnight. The reaction mixture was quenched with water (250 mL) and washed twice with diethyl ether. The aqueous layer was cooled to 0° C. and acidified to pH 4-5 using 1N aqueous HCl. The aqueous layer was extracted twice with diethyl ether and the combined organic extracts were dried over MgSO$_4$, filtered and concentrated under reduced pressure to provide intermediate 7-b as a beige oil.

Step 2: Intermediate 7-c

To a solution of ethyl 2-chloro-3-oxopropanoate, 7-b (34.7 g, 230 mmol) in toluene (250 ml) was added thioacetamide (26.0 g, 346.0 mmol). The reaction was stirred at 90° C. overnight and then cooled to room temperature, diluted with water (300 mL) and then neutralized to pH=7 with saturated aqueous NaHCO$_3$. Ethyl acetate was added, the organic layer was separated, washed with brine, dried over MgSO$_4$, filtered and concentrated under reduced pressure. Purification by silica gel chromatography provided intermediate 7-c as a beige oil.

Step 3: Intermediate 7-d

To a solution of intermediate 7-c (22.2 g, 130.0 mmol) in THF (430 ml) cooled to 0° C. was added a 1.0 M solution LiAlH$_4$ in THF (91.0 ml, 91.0 mmol). The solution was slowly warmed to room temperature and stirred for 2 hours. Water (3.5 ml) was slowly added, followed by 3.5 ml 15% NaOH (3.5 ml) and water (10.5 ml) and the mixture was stirred for 1 hour. The reaction was filtered through celite and the filtrate collected. Volatiles were removed in vacuo to provide intermediate 7-d as a yellow oil.

Synthesis of Intermediate 8-e

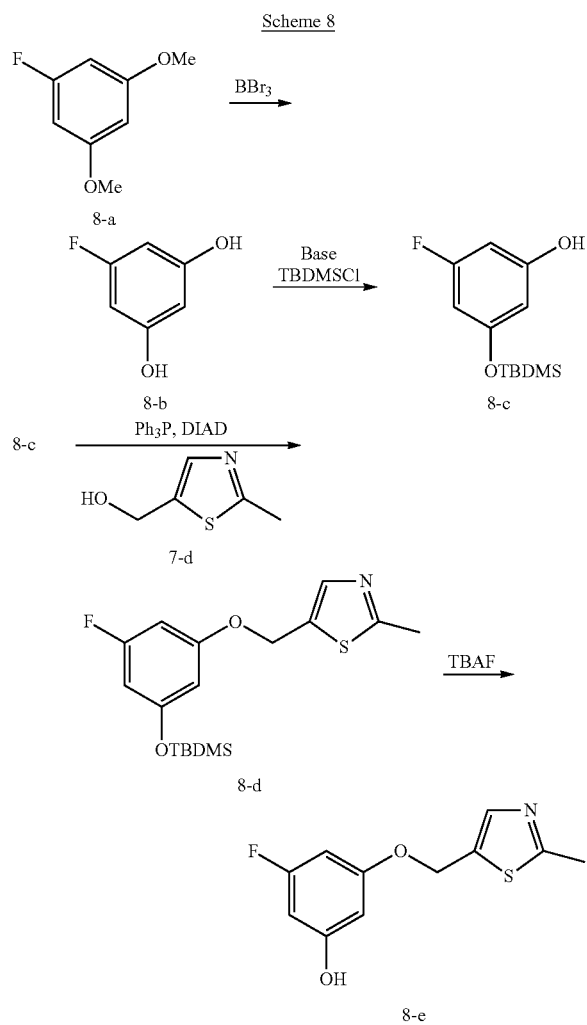

Step 1: Intermediate 8-b

To a solution of 1-fluoro-3,5-dimethoxybenzene (12.5 g, 80.0 mmol) in dichloromethane (80 ml), cooled to 0° C., was added a 1.0 M solution of BBr₃ in dichloromethane (200 ml, 200 mmol), dropwise over a 30 minutes period. The reaction was stirred for 1 hour at 0° C. and then slowly warmed to room temperature and stirred for 18 hours. The reaction was cooled to 0° C. and quenched by slow addition of MeOH and water. After stirring at room temperature for 1 hour the mixture was filtered and volatiles were removed in vacuo. The solid was washed twice with ethyl acetate; the filtrate was concentrated in vacuo to provide intermediate 8-b as an orange solid.

Step 2: Intermediate 8-c

To a solution of intermediate 8-b (10.25 g, 80.0 mmol) in DMF (50 ml), cooled to 0° C., was added imidazole (5.99 g, 88.0 mmol) and tert-butylchlorodimethylsilane (13.27 g, 88.0 mmol). The reaction was then stirred at room temperature overnight. A saturated aqueous solution of ammonium chloride and ethyl acetate were added; the organic layer was separated, washed 3 times with a saturated aqueous solution of ammonium chloride and brine, dried over MgSO₄, filtered and concentrated under reduced pressure. Purification by silica gel chromatography provided intermediate 8-c as a yellow oil.

Step 3: Intermediate 8-d

To a solution of intermediate 8-c (1.0 g, 105.0 mmol) and intermediate 7-d (352 mg, 2.73 mmol) in THF (20 ml) were sequentially added triphenylphosphine (1.07 g, 4.1 mmol) and DIAD (796 μl, 4.1 mmol) at room temperature. The reaction was then stirred at room temperature for 1 hour. Volatiles were removed under reduced pressure. Purification by silica gel chromatography provided intermediate 8-d as a yellow oil.

Step 4: Intermediate 8-e

To a solution of intermediate 8-d (750 mg, 1.57 mmol) in THF (20 ml) was added a 1.0 M solution of TBAF in THF (1.72 ml, 1.72 mmol) and the reaction was stirred at room temperature for 1 hour. A saturated aqueous solution of ammonium chloride and ethyl acetate were added, the organic layer was separated, washed with brine, dried over MgSO₄, filtered and concentrated under reduced pressure. Diethyl ether was added to the residue; a precipitate formed and was collected by filtration to provide intermediate 8-e as a white solid.

Synthesis of Intermediate 9-d

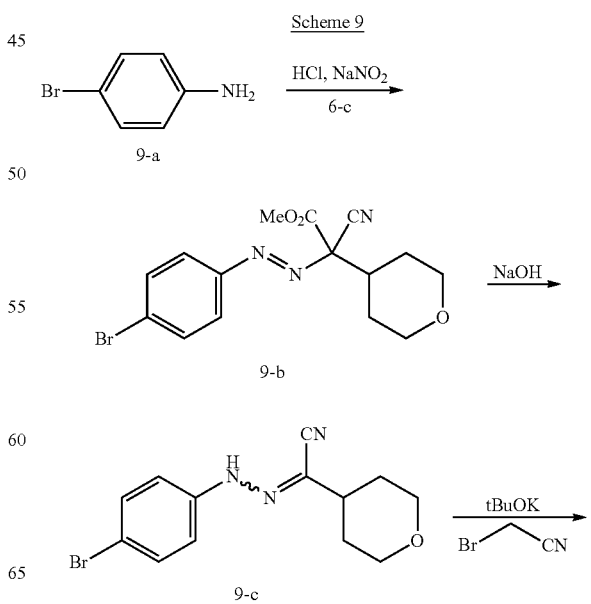

21
-continued

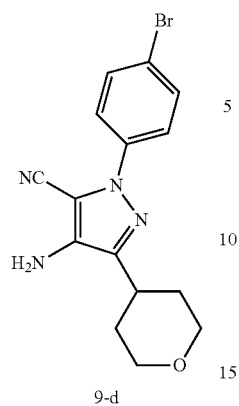

9-d

Step 1: Intermediate 9-b

To a solution of 4-bromoaniline (8.43 g, 49.0 mmol) in 1N aqueous HCl (123 ml) was added dropwise 1.0 M aqueous sodium nitrite (49.0 ml g, 49.0 mmol) at room temperature. The mixture was stirred for 1 hour and then added dropwise to an ice cooled solution of intermediate 6-c (4.5 g, 24.56 mmol) in ethanol (34.30 ml) and water (457 mL). The pH was maintained at 7 by adding sodium acetate portion wise. The mixture was stirred at 0° C. for 3 hours and then at room temperature until completion. A saturated aqueous solution of ammonium chloride and ethyl acetate were added, the organic layer was separated, washed with brine, dried over MgSO$_4$, filtered and concentrated under reduced pressure to provide intermediate 9-b as a beige oil.

Step 2: Intermediate 9-c

To a solution of intermediate 9-b (10.0 g, 27.3 mmol) in THF (273 ml), cooled to 0° C., was added 10N aqueous NaOH (68.3 ml, 683.0 mmol) and the reaction was stirred at room temperature for 2 hours. A saturated aqueous solution of ammonium chloride and ethyl acetate were added, the organic layer was separated, washed with 10% citric acid, saturated aqueous NaHCO$_3$ and brine, dried over MgSO$_4$, filtered and concentrated under reduced pressure. Purification by silica gel chromatography provided intermediate 9-c as a yellow solid.

Step 3: Intermediate 9-d

To a solution of intermediate 9-c (4.0 g, 12.98 mmol) and bromoacetonitrile (995 μl, 14.28 mmol) in tert-butanol (64.9 ml), cooled to 0° C. was added a 1.0 M solution of potassium tert-butoxide in tert-butanol (27.3 ml, 27.3 mmol) and the reaction was stirred at room temperature for 2 hours. A saturated aqueous solution of ammonium chloride and ethyl acetate were added, the organic layer was separated, washed with brine, dried over MgSO$_4$, filtered and concentrated under reduced pressure. Purification by silica gel chromatography provided intermediate 9-d as a beige solid.

22
Synthesis of Compound 3

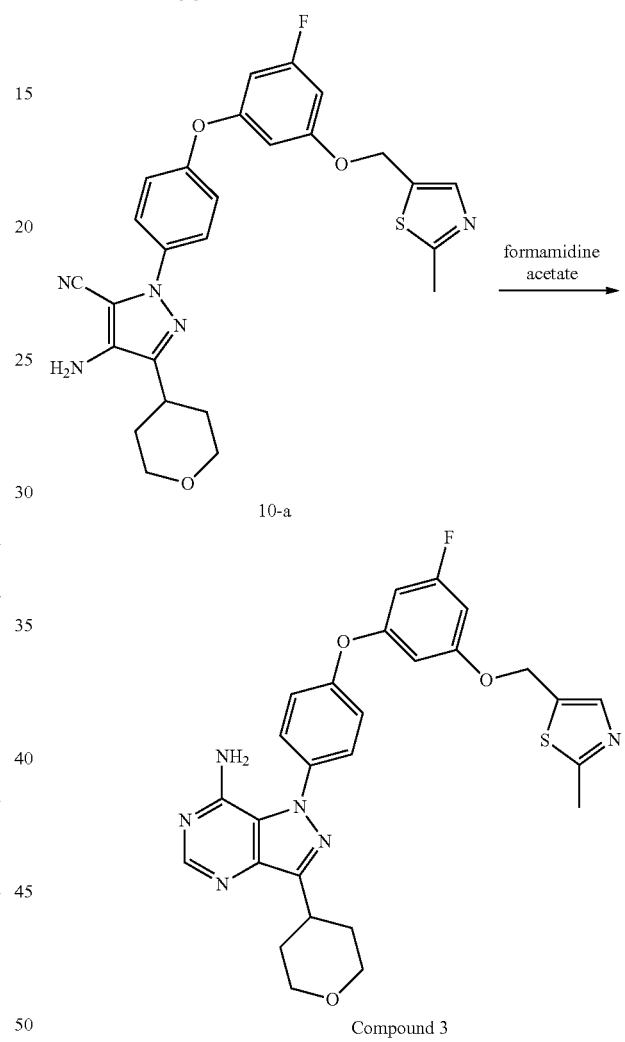

Step 1: Intermediate 10-a

To a solution of intermediate 8-e (138 mg, 0.57 mmol) and intermediate 9-d (200 mg, 0.57 mmol) in 1,4-dioxane were sequentially added N,N-dimethylglycine (36 mg, 0.35 mmol), cesium carbonate (375 mg, 1.15 mmol) and copper (I) iodide (22 mg, 0.11 mmol). The reaction was stirred at reflux overnight and then cooled to room temperature. Water and ethyl acetate were added, the organic layer was separated, washed with brine, dried over MgSO$_4$, filtered and concentrated under reduced pressure to provide intermediate 10-a as a brown solid.

Step 13: Compound 3

To a solution of intermediate 10-a (291 mg, 0.57 mmol) in EtOH (6.0 ml) was added formamidine acetate (479 mg, 4.60 mmol) and the reaction was stirred at 80° C. for 3 hours and then cooled to room temperature. Volatiles were removed under reduced pressure. Purification by reverse phase chromatography eluting with a 0.1% aqueous HCl/methanol gradient provided compound 3·2HCl as a white solid. MS (m/z) M+H=533.1

Synthesis of Intermediate 11-d

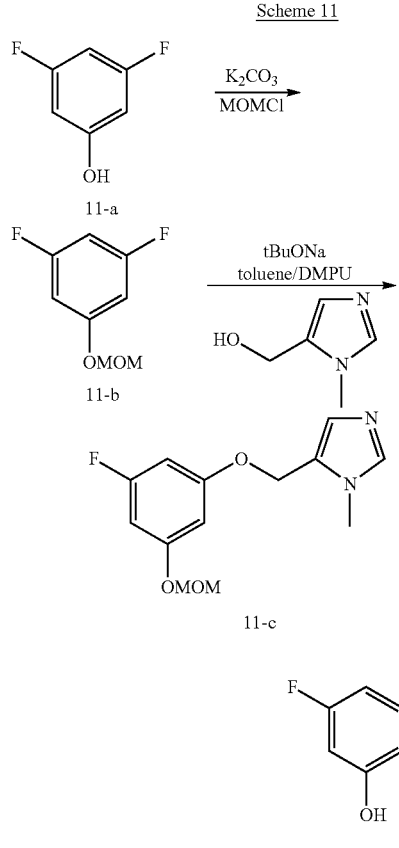

Step 1: Intermediate 11-b

To a solution of 3,5-difluorophenol (15.0 g, 115 mmol) in acetone (200 ml) was added $K_2CO_3$ (23.90 g, 173 mmol) and chloromethyl methyl ether (15.85 g, 127 mmol). The reaction was then stirred at room temperature overnight and filtered. The filtrate was concentrated under reduced pressure to provide intermediate 11-b as a colorless oil.

Step 2: Intermediate 11-c

To a solution of (1-methyl-1H-imidazol-5-yl) methanol (3.1 g, 27.6 mmol) and intermediate 11-b (4.01 g, 23.04 mmol) in toluene (25.0 ml) and DMPU (25.0 ml) was added sodium 2-methylpropan-2-olate (4.43 g, 46.1 mmol). The reaction was stirred overnight at 80° C. and then cooled to room temperature. A saturated aqueous solution of ammonium chloride and ethyl acetate were added, the organic layer was separated, washed twice with a saturated aqueous solution of ammonium chloride and brine, dried over $MgSO_4$, filtered and concentrated in vacuo. Purification by silica gel chromatography provided intermediate 11-c as a beige oil.

Step 3: Intermediate 11-d

To a solution of intermediate 11-c (3.2 g, 12.02 mmol) in MeOH (25.0 ml) was added 4N HCl in 1,4-dioxane (10.95 ml, 361.0 mmol) and the reaction was stirred overnight at room temperature. Volatiles were removed in vacuo. Diethyl ether was added to the residue; a precipitate formed and was collected by filtration to provide intermediate 11-d.HCl as a white solid.

Synthesis of Compound 4

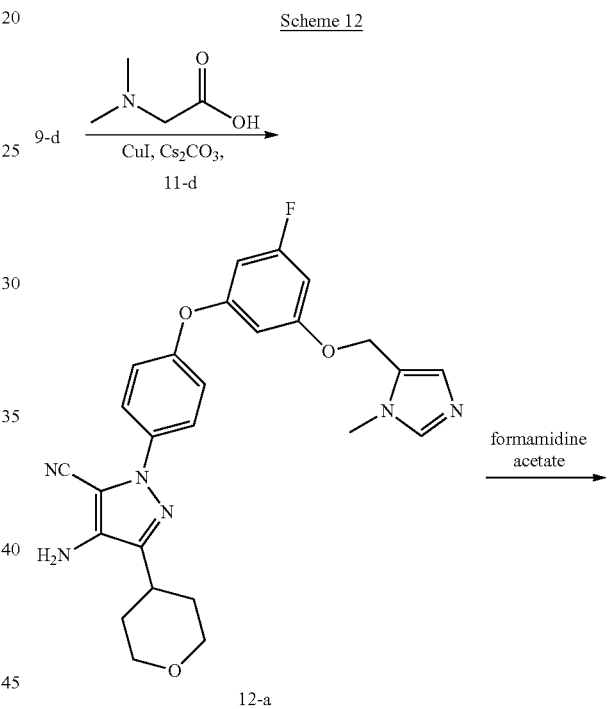

Scheme 12

Step 1: Intermediate 12-a

To a solution of intermediate 11-d (120 mg, 0.54 mmol) and intermediate 9-d (187 mg, 0.54 mmol) in 1,4-dioxane were sequentially added N,N-dimethylglycine (167 mg, 1.62 mmol), cesium carbonate (528 mg, 1.62 mmol) and copper (I) iodide (103 mg, 0.54 mmol). The reaction was stirred at reflux overnight and then cooled to room temperature. Ethyl acetate was added, the reaction was filtered over celite. Water was added to the filtrate, the organic layer was separated, washed with brine, dried over MgSO$_4$, filtered and concentrated under reduced pressure to provide intermediate 12-a as a brown solid.

Step 2: Compound 4

To a solution of intermediate 12-a (250 mg, 0.51 mmol) in EtOH (6.0 ml) was added formamidine acetate (426 mg, 4.09 mmol) and the reaction was stirred at 80° C. for 3 hours and then cooled to room temperature. Volatiles were removed under reduced pressure. Purification by reverse phase chromatography eluting with a 0.1% aqueous HCl/methanol gradient provided compound 4·2HCl as a white solid. MS (m/z) M+H=516.2

Synthesis of Intermediate 13-c

Scheme 13

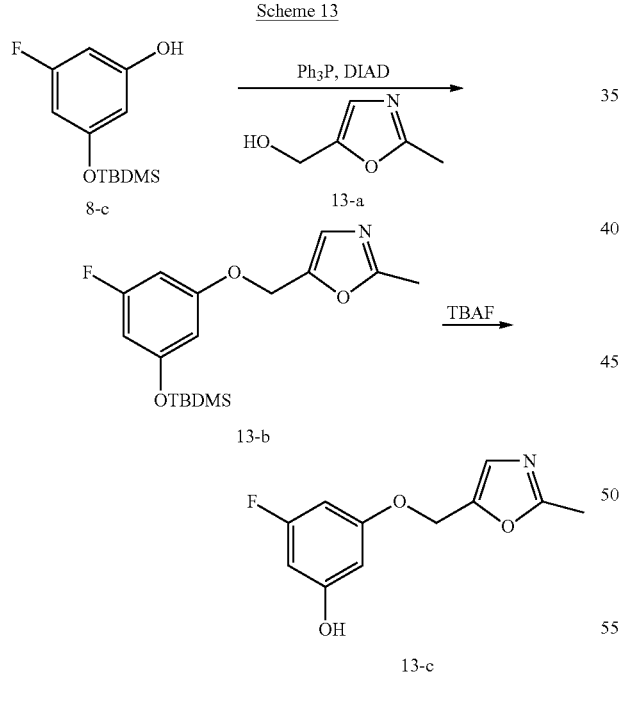

Step 1: Intermediate 13-b

To a solution of intermediate 8-c (1.43 g, 5.89 mmol) and (2-methyloxazol-5-yl)methanol (1.0 g, 8.84 mmol) in THF (20 ml) were sequentially added triphenylphosphine (2.32 g, 8.84 mmol) and DIAD (1.72 ml, 8.84 mmol) at room temperature. The reaction was then stirred at room temperature for 1 hour. Volatiles were removed under reduced pressure. Purification by silica gel chromatography provided intermediate 13-b as a yellow oil.

Step 2: Intermediate 13-c

To a solution of intermediate 13-b (1.10 g, 3.26 mmol) in THF (32 ml) was added a 1.0 M solution of TBAF in THF (3.59 ml, 3.59 mmol) and the reaction was stirred at room temperature for 1 hour. A saturated aqueous solution of ammonium chloride and ethyl acetate were added, the organic layer was separated, washed with brine, dried over MgSO$_4$, filtered and concentrated under reduced pressure. Purification by silica gel chromatography provided intermediate 13-c as a white solid.

Synthesis of Compound 5

Scheme 14

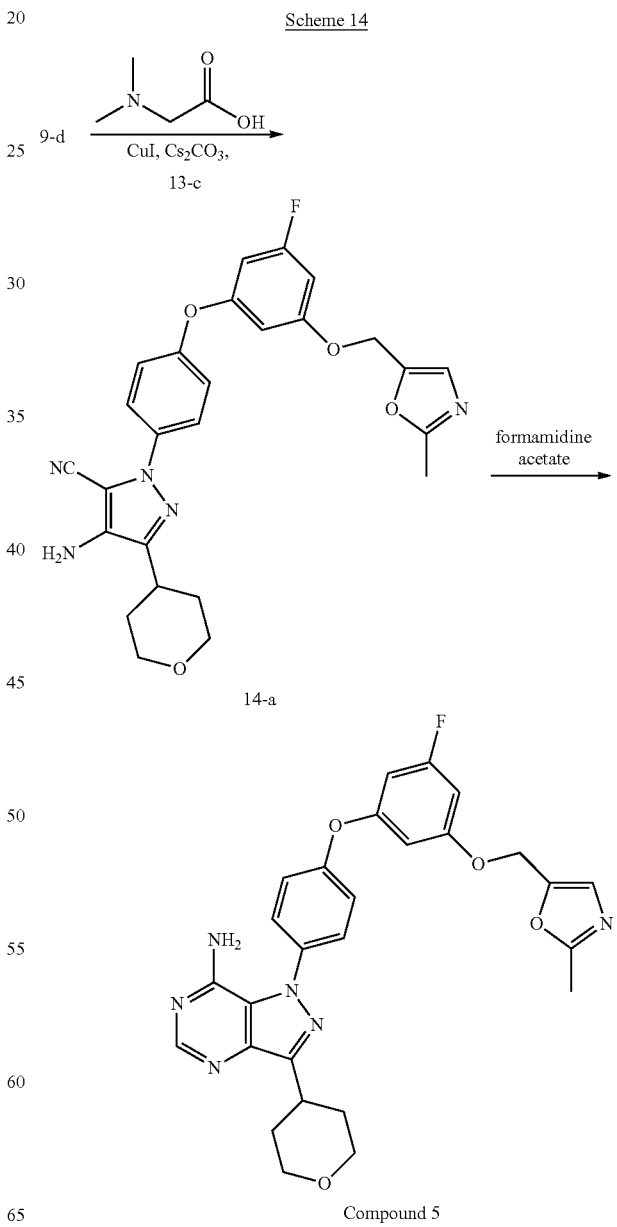

Compound 5

Step 1: Intermediate 14-a

To a solution of intermediate 13-c (129 mg, 0.57 mmol) and intermediate 9-d (200 mg, 0.57 mmol) in 1,4-dioxane were sequentially added N,N-dimethylglycine (36 mg, 0.34 mmol), cesium carbonate (375 mg, 1.15 mmol) and copper (I) iodide (22 mg, 0.11 mmol). The reaction was stirred at reflux overnight and then cooled to room temperature. Ethyl acetate was added, the reaction was filtered over celite. Water was added to the filtrate, the organic layer was separated, washed with brine, dried over MgSO$_4$, filtered and concentrated under reduced pressure to provide intermediate 14-a as a brown solid.

Step 2: Compound 5

To a solution of intermediate 14-a (384 mg, 0.78 mmol) in EtOH (7.8 ml) was added formamidine acetate (653 mg, 6.28 mmol) and the reaction was stirred at 80° C. for 3 hours and then cooled to room temperature. Volatiles were removed under reduced pressure. Purification by reverse phase chromatography eluting with a 0.1% aqueous HCl/methanol gradient provided compound 5·2HCl as a white solid. MS (m/z) M+H=517.2

Synthesis of Intermediate 15-b

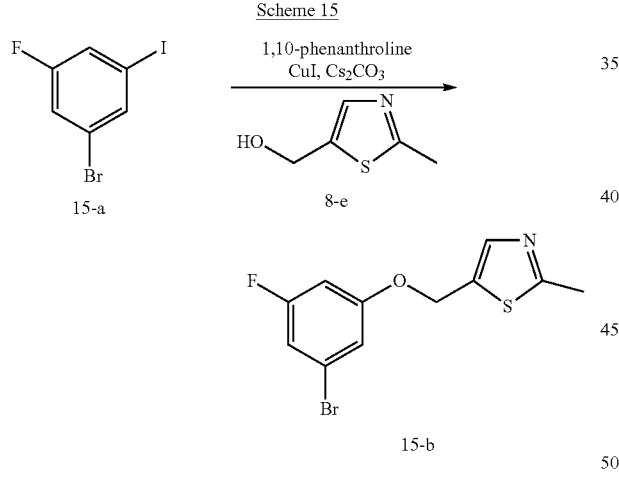

To a solution of 1-bromo-3-fluoro-5-iodobenzene 15-a (7.52 g, 25.0 mmol) in 1,4-dioxane (12.50 ml) was added (2-methylthiazol-5-yl)methanol 8-e (3.55 g, 27.5 mmol), 1,10-phenanthroline (901 mg, 5.0 mmol), copper (I) iodide (476 mg, 2.50 mmol) and cesium carbonate (11.40 g, 35.0 mmol). The reaction was stirred at 110° C. for 2 days and then cooled to room temperature, diluted with ethyl acetate and filtered over celite. A saturated aqueous solution of ammonium chloride was added to the filtrate, the organic layer was separated, and the aqueous phase was extracted twice with ethyl acetate. The combined organic extracts were washed with brine, dried over MgSO$_4$, filtered and concentrated under reduced pressure. Purification by silica gel chromatography provided intermediate 15-b as a beige oil.

Synthesis of Intermediate 16-b

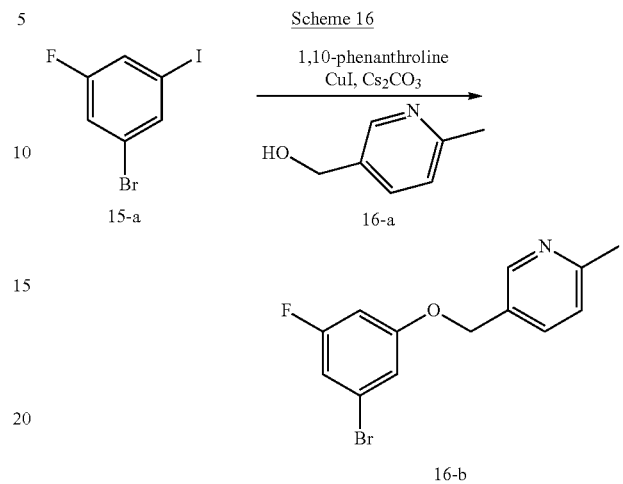

To a solution of 1-bromo-3-fluoro-5-iodobenzene 15-a (5.0 g, 16.62 mmol) in toluene (8.3 ml) was added (6-methylpyridin-3-yl) methanol 16-a (2.25 g, 18.28 mmol), 1,10-phenanthroline (599 mg, 3.32 mmol), copper (I) iodide (316 mg, 1.66 mmol) and cesium carbonate (7.58 g, 23.26 mmol). The reaction was stirred at 110° C. for 2 days and then cooled to room temperature, diluted with ethyl acetate and filtered over celite. A saturated aqueous solution of ammonium chloride was added to the filtrate, the organic layer was separated, and the aqueous phase was extracted twice with ethyl acetate. The combined organic extracts were washed with brine, dried over MgSO$_4$, filtered and concentrated under reduced pressure. Purification by silica gel chromatography provided intermediate 16-b as a beige solid.

Synthesis of Intermediate 17-b

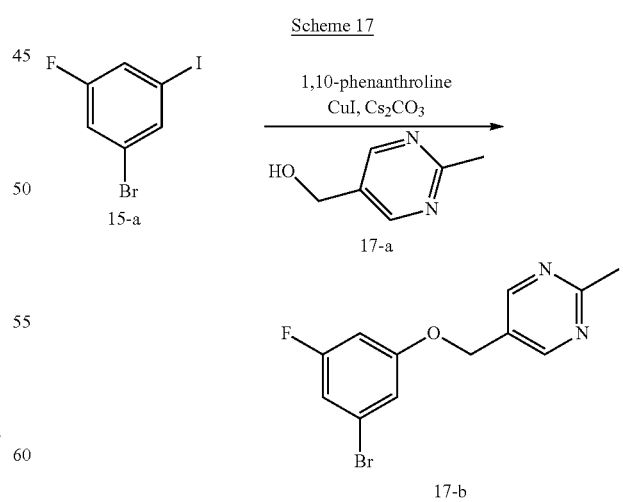

To a solution of 1-bromo-3-fluoro-5-iodobenzene 15-a (5.0 g, 16.62 mmol) in toluene (8.3 ml) was added (2-methylpyrimidin-5-yl)methanol (2.26 g, 18.28 mmol), 1,10-phenanthroline (599 mg, 3.32 mmol), copper (I) iodide (316 mg, 1.66 mmol) and cesium carbonate (7.58 g, 23.26 mmol). The reaction was stirred at 110° C. for 2 days and then cooled to room temperature, diluted with ethyl acetate and filtered over celite. A saturated aqueous solution of ammonium chloride was added to the filtrate, the organic layer was separated, and the aqueous phase was extracted twice with ethyl acetate. The combined organic extracts were washed with brine, dried over MgSO$_4$, filtered and concentrated under reduced pressure. Purification by silica gel chromatography provided intermediate 17-b as a beige solid.

Synthesis of Intermediate 18-b

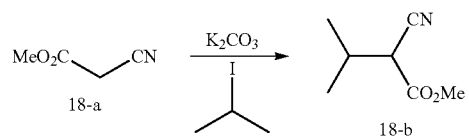

Scheme 18

To a solution of ethyl 2-cyanoacetate 18-a (11.42 g, 101.0 mmol) in acetone (153.0 ml) was added potassium carbonate (20.94 g, 152.0 mmol) and 2-iodopropane (29.2 g, 172.0 mmol). The reaction mixture was heated to reflux for 2 days, cooled to room temperature and diluted in a 1:1 mixture of ethyl acetate/hexanes. Water was added, the organic layer was separated, washed with brine, dried over MgSO$_4$, filtered and concentrated under reduced pressure to provide intermediate 18-b as a colorless oil.

Synthesis of Intermediate 19-e

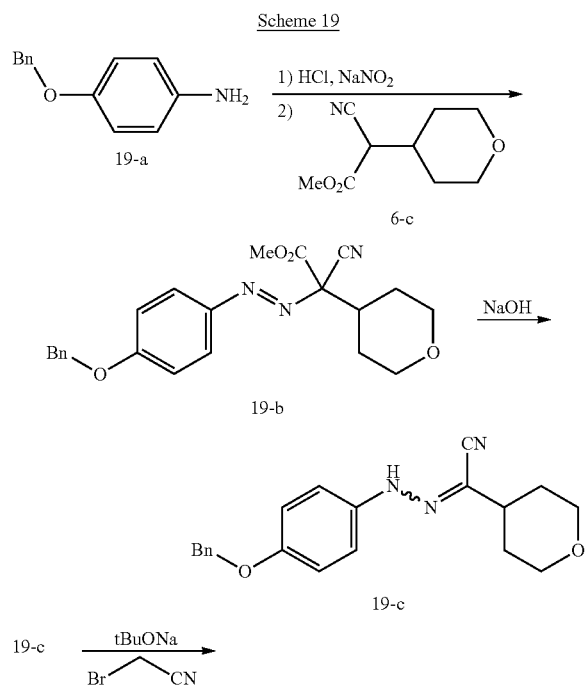

Scheme 19

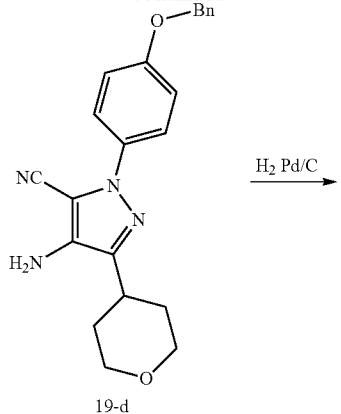

19-d

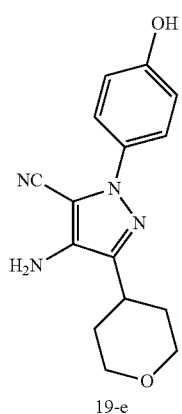

19-e

Step 1: Intermediate 19-b

To a solution of 4-(benzyloxy)aniline hydrochloride 19-a (14.3 g, 60.8 mmol) in 1N HCl (51.4 ml) was added dropwise a 1.0 M solution of sodium nitrite in water (76.0 ml, 76.0 mmol) at room temperature, the mixture was stirred for 1 hour, filtered and then added dropwise to an ice cooled solution of intermediate 6-c (10.0 g, 50.7 mmol) in ethanol (13.7 ml) and water (188.0 mL). The PH was maintained at 7 by adding potassium acetate portion wise. The mixture was stirred at 0° C. for 3 hours and room temperature overnight. A saturated aqueous solution of ammonium chloride and ethyl acetate were added, the organic layer was separated, washed with brine, dried over MgSO$_4$, filtered and concentrated under reduced pressure to provide intermediate 19-b as a beige oil.

Step 2: Intermediate 19-c

To a solution of intermediate 19-b (20.3 g, 49.8 mmol) in a 1:1 mixture of 1,4-dioxane/water (249.0 ml) cooled to 0° C. was added NaOH 10N (100.0 ml, 996.0 mmol) and the reaction was stirred at room temperature for 1 hour. A saturated aqueous solution of ammonium chloride and ethyl acetate were added, the organic layer was separated, washed with brine, dried over MgSO$_4$, filtered and concentrated under reduced pressure. Purification by silica gel chromatography provided intermediate 19-c as a yellow solid.

Step 3: Intermediate 19-d

To a solution of intermediate 19-c (6.5 g, 19.4 mmol) in tert-butanol (97.0 ml) was added a 1.0 M solution of potassium tert-butoxide in tert-butanol (40.7 ml, 40.7 mmol). After stirring for 15 minutes, bromoacetonitrile (3.37 ml, 48.4 mmol) was added and the reaction was stirred for 3 hours at room temperature. A saturated aqueous solution of ammonium chloride and ethyl acetate were added, the organic layer was separated, the aqueous phase was extracted with ethyl acetate, the combined organic extracts were washed with brine, dried over MgSO₄, filtered and concentrated under reduced pressure. Purification by silica gel chromatography provided intermediate 19-d as a beige foam.

Step 4: Intermediate 19-e

To a solution of intermediate 19-d (6.5 g, 17.36 mmol) in ethyl acetate and stirred under nitrogen was added 10% Pd/C (3.69 g, 1.73 mmol). The reaction mixture was purged with H₂ and stirred for 1 hour under 1 atm of hydrogen. The reaction was then filtered through celite and the filtrate was concentrated in vacuo. Volatiles were removed under reduced pressure to provide intermediate 19-e as a yellow solid.

Synthesis of Intermediate 20-d

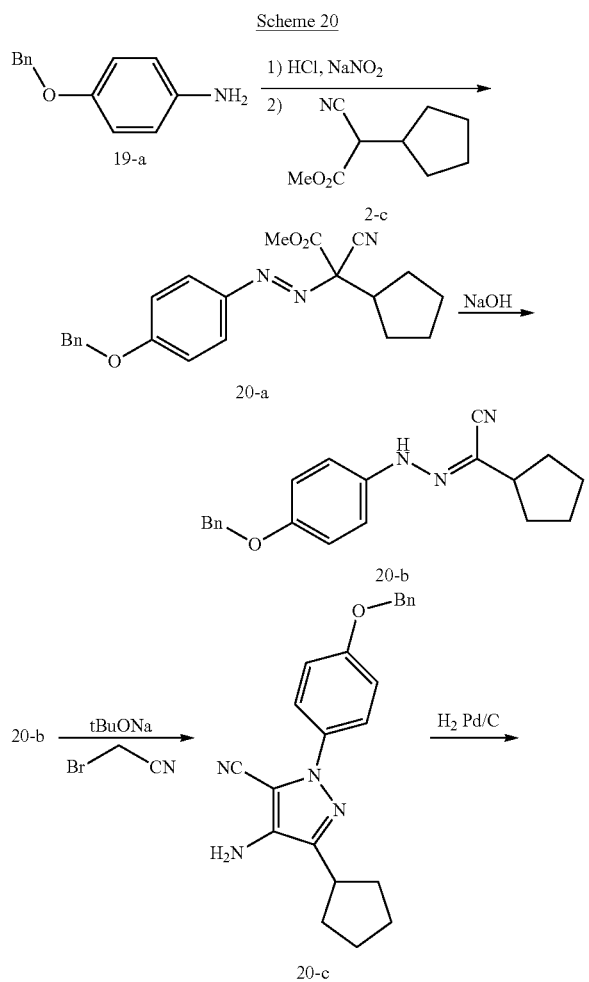

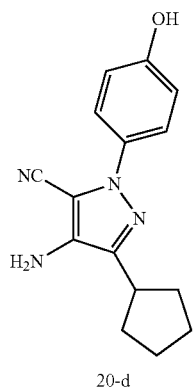

Step 1: Intermediate 20-a

To a solution of 4-(benzyloxy)aniline hydrochloride 19-a (10.0 g, 42.4 mmol) in 1N HCl (60.6 ml) was added dropwise a 1.0 M solution of sodium nitrite (41.9 ml, 41.9 mmol) in water at room temperature, the mixture was stirred for 1 hour, filtered and then added dropwise to an ice cooled solution of intermediate 2-c (5.0 g, 29.9 mmol) in ethanol (16.2 ml) and water (222.0 mL). The PH was maintained at 7 by adding potassium acetate portion wise. The mixture was stirred at 0° C. for 3 hours and room temperature for 1 hour. A saturated aqueous solution of ammonium chloride and ethyl acetate were added, the organic layer was separated, washed with brine, dried over MgSO₄, filtered and concentrated under reduced pressure to provide intermediate 20-a as a beige oil.

Step 2: Intermediate 20-b

To a solution of intermediate 20-a (10.0 g, 26.5 mmol) in a 1:1 mixture of 1,4-dioxane/water (265.0 ml) cooled to 0° C. was added NaOH 10N (53.0 ml, 530.0 mmol) and the reaction was stirred at room temperature for 1 hour. A saturated aqueous solution of ammonium chloride and ethyl acetate were added, the organic layer was separated, washed with brine, dried over MgSO₄, filtered and concentrated under reduced pressure. Purification by silica gel chromatography provided intermediate 20-b as a yellow solid.

Step 3: Intermediate 20-c

To a solution of intermediate 20-b (8.3 g, 28.8 mmol) and bromoacetonitrile (4.33 ml, 62.1 mmol) in tert-butanol (141.0 ml) was added a 1.0 M solution of sodium tert-butoxide in tert-butanol (56.4 ml, 56.4 mmol). The reaction was slowly warmed to room temperature and stirred for 2 hours. A saturated aqueous solution of ammonium chloride and ethyl acetate were added, the organic layer was separated, washed with brine, dried over MgSO₄, filtered and concentrated under reduced pressure. Purification by silica gel chromatography provided intermediate 20-c as a beige foam.

Step 4: Intermediate 20-d

To a solution of intermediate 20-c (3.72 g, 10.38 mmol) in ethyl acetate and stirred under nitrogen was added 10% Pd/C (2.20 g, 1.03 mmol). The reaction mixture was purged with H₂ and stirred for 1 hour under 1 atm of hydrogen. The reaction was then filtered through celite and the filtrate was concentrated in vacuo. Volatiles were removed under reduced pressure to provide intermediate 20-d as a yellow solid.

Synthesis of Intermediate 21-d

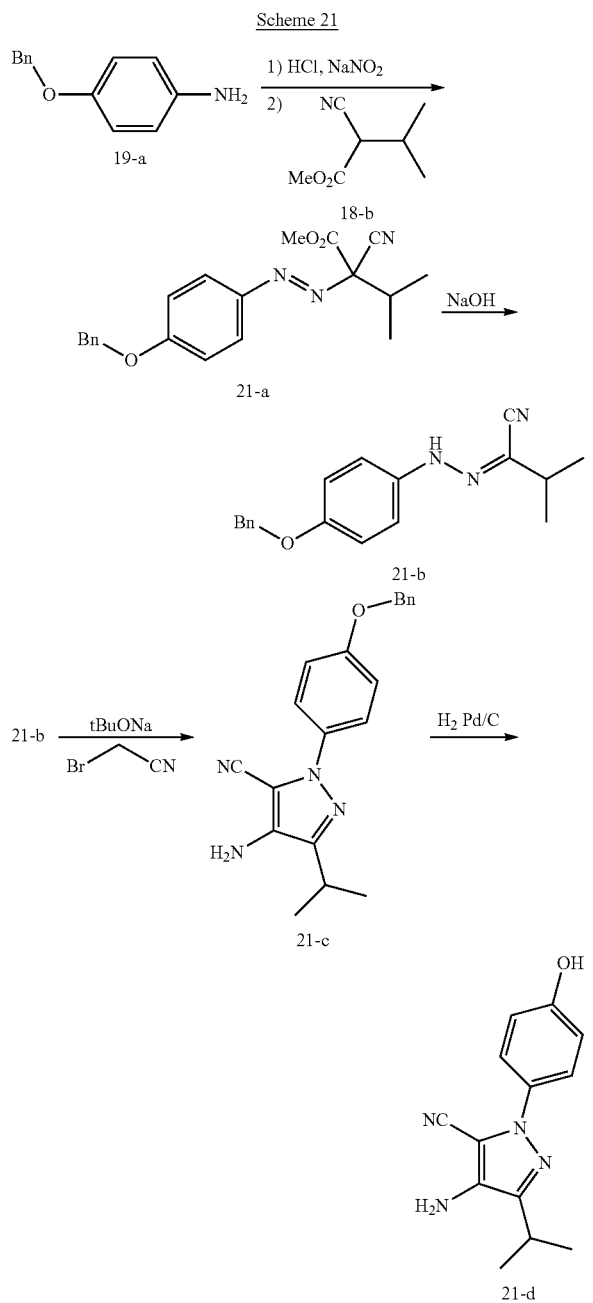

Step 1: Intermediate 21-a

To a solution of 4-(benzyloxy)aniline hydrochloride 19-a (20.0 g, 85.0 mmol) in 1N HCl (71.8 ml) was added dropwise a 1.0 M solution of sodium nitrite (99.0 ml, 99.0 mmol) in water at room temperature, the mixture was stirred for 1 hour, filtered and then added dropwise to an ice cooled solution of intermediate 18-b (10.0 g, 70.8 mmol) in ethanol (19.1 ml) and water (263.0 mL). The PH was maintained at 7 by adding sodium acetate portion wise. The mixture was stirred at 0° C. for 3 hours and room temperature overnight. A saturated aqueous solution of ammonium chloride and ethyl acetate were added, the organic layer was separated, washed with brine, dried over $MgSO_4$, filtered and concentrated under reduced pressure to provide intermediate 21-a as a beige oil.

Step 2: Intermediate 21-b

To a solution of intermediate 21-a (24.0 g, 68.3 mmol) in a 1:1 mixture of 1,4-dioxane/water (341.0 ml) cooled to 0° C. was added NaOH 10N (137.0 ml, 1366.0 mmol) and the reaction was stirred at room temperature for 1 hour. A saturated aqueous solution of ammonium chloride and ethyl acetate were added, the organic layer was separated, washed with brine, dried over $MgSO_4$, filtered and concentrated under reduced pressure to provide intermediate 21-b as a yellow solid.

Step 3: Intermediate 21-c

To an ice cooled solution of intermediate 21-b (8.28 g, 28.2 mmol) in tert-butanol (141.0 ml) was added a 1.0 M solution of sodium tert-butoxide in tert-butanol (56.4 ml, 56.4 mmol). After stirring for 15 minutes, bromoacetonitrile (4.33 ml, 62.1 mmol) was added; the reaction was slowly warmed to room temperature and stirred for 2 hours. A saturated aqueous solution of ammonium chloride and ethyl acetate were added, the organic layer was separated, washed with brine, dried over $MgSO_4$, filtered and concentrated under reduced pressure. Purification by silica gel chromatography provided intermediate 21-c as a yellow solid.

Step 4: Intermediate 21-d

To a solution of intermediate 21-c (5.84 g, 17.57 mmol) in ethyl acetate and stirred under nitrogen was added 10% Pd/C (1.87 g, 0.87 mmol). The reaction mixture was purged with $H_2$ and stirred for 1 hour under 1 atm of hydrogen. The reaction was then filtered through celite and the filtrate was concentrated in vacuo. Purification by silica gel chromatography provided intermediate 21-d as a yellow solid.

Synthesis of Compound 14

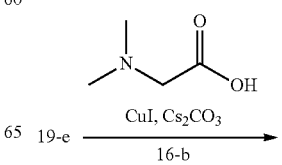

36

Synthesis of Compound 15

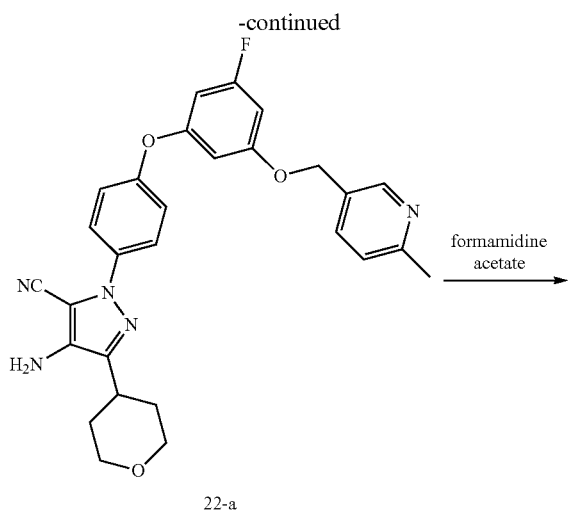

22-a

Compound 14

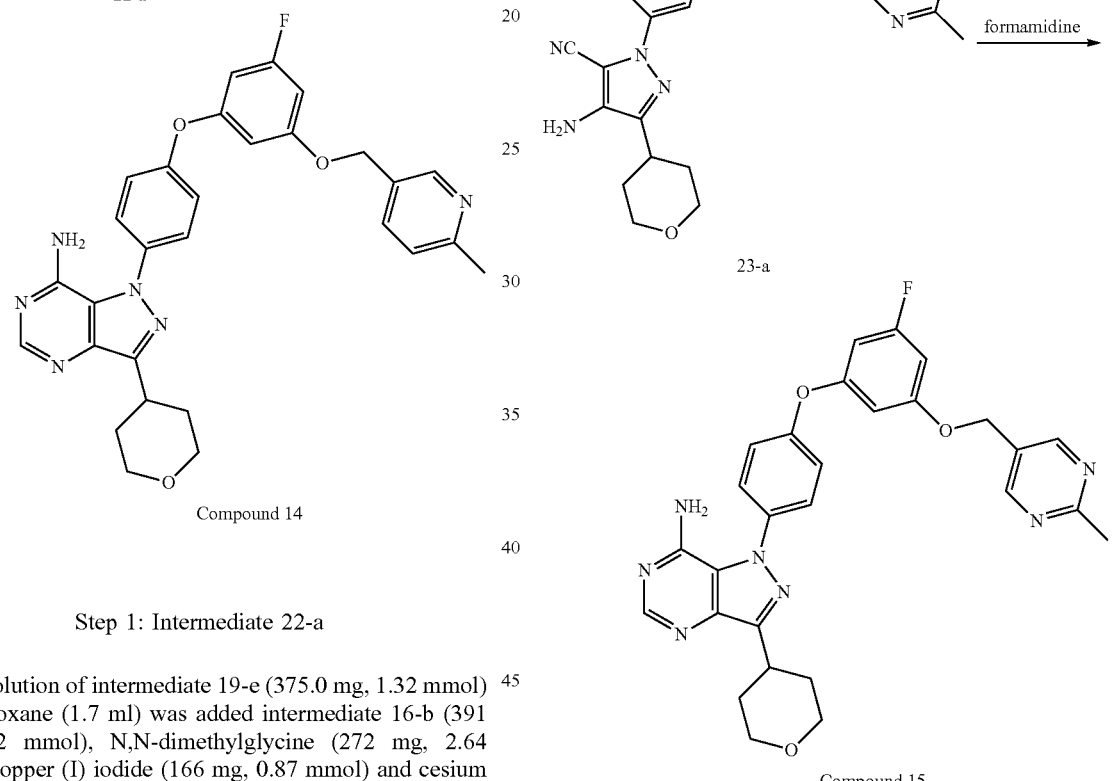

23-a

Compound 15

Step 1: Intermediate 22-a

To a solution of intermediate 19-e (375.0 mg, 1.32 mmol) in 1,4-dioxane (1.7 ml) was added intermediate 16-b (391 mg, 1.32 mmol), N,N-dimethylglycine (272 mg, 2.64 mmol), copper (I) iodide (166 mg, 0.87 mmol) and cesium carbonate (1.72 g, 5.28 mmol). The reaction was heated in a sealed tube at 110° C. overnight and then cooled to room temperature, diluted with ethyl acetate and filtered over celite. Volatiles were removed under reduced pressure. Purification by silica gel chromatography provided intermediate 22-a as a beige foam.

Step 2: Compound 14

To a solution of intermediate 22-a (275 mg, 0.55 mmol) in methanol (5.5 ml) was added formamidine acetate (401 mg, 3.85 mmol) and the reaction was stirred at reflux overnight and then cooled to room temperature. Volatiles were removed under reduced pressure. Purification by reverse phase chromatography eluting with a 0.1% aqueous HCl/methanol gradient provided compound 14·2HCl as a white solid. MS (m/z) M+H=527.2

Step 1: Intermediate 23-a

To a solution of intermediate 19-e (375 mg, 1.32 mmol) in 1,4-dioxane (1.7 ml) was added intermediate 17-b (392 mg, 1.32 mmol), N,N-dimethylglycine (272 mg, 2.64 mmol), copper (I) iodide (166 mg, 0.87 mmol) and cesium carbonate (1.72 g, 5.28 mmol). The reaction was heated in a sealed tube at 110° C. overnight and then cooled to room temperature, diluted with ethyl acetate and filtered over celite. Volatiles were removed under reduced pressure. Purification by silica gel chromatography provided intermediate 23-a as a beige foam.

Step 2: Compound 15

To a solution of intermediate 23-a (260 mg, 0.52 mmol) in methanol (5.2 ml) was added formamidine acetate (541 mg, 5.19 mmol) and the reaction was stirred at reflux overnight and then cooled to room temperature. Volatiles were removed under reduced pressure. Purification by reverse phase chromatography eluting with a 0.1% aqueous HCl/methanol gradient provided compound 15·2HCl as a white solid. MS (m/z) M+H=528.1

Synthesis of Compound 7

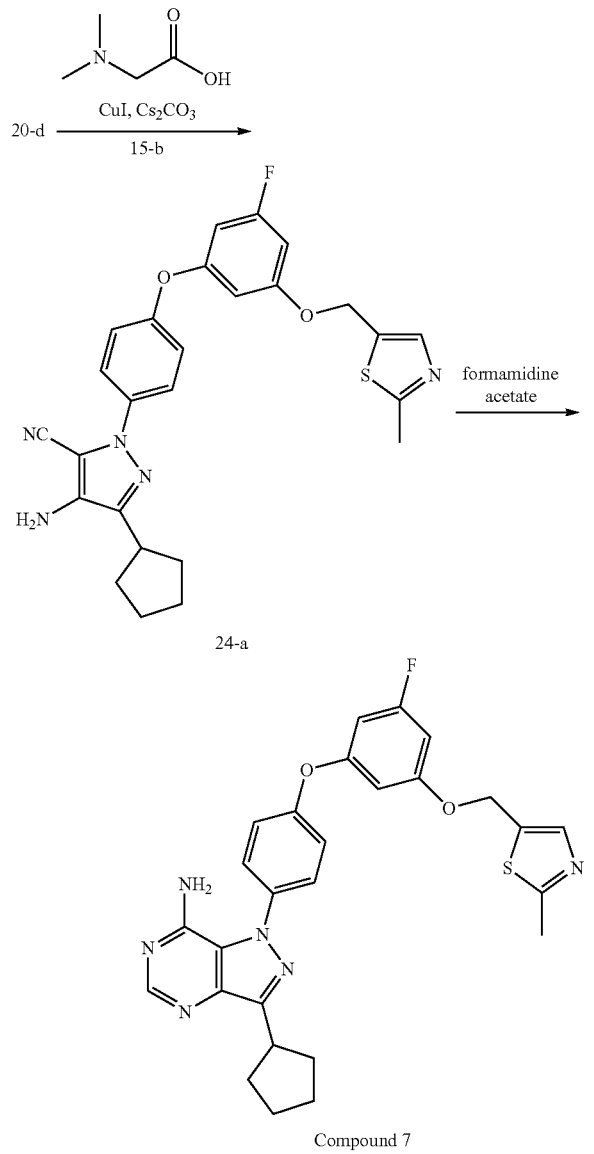

Step 2: Intermediate 24-a

To a solution of intermediate 20-d (533.0 mg, 1.98 mmol) in 1,4-dioxane (1.0 ml) was added intermediate 15-b (600 mg, 1.98 mmol), N,N-dimethylglycine (410 mg, 3.97 mmol), copper (I) iodide (250 mg, 1.31 mmol) and cesium carbonate (2.59 g, 7.94 mmol). The reaction was heated in a sealed tube at 110° C. overnight and then cooled to room temperature, diluted with ethyl acetate and filtered over celite. Volatiles were removed under reduced pressure. Purification by silica gel chromatography provided intermediate 24-a as a beige oil.

Step 2: Compound 7

To a solution of intermediate 24-a (470.0 mg, 0.96 mmol) in ethanol (9.60 ml) was added formamidine acetate (800 mg, 7.68 mmol) and the reaction was stirred at 80° C. for 3 hours and then cooled to room temperature. Volatiles were removed under reduced pressure. Purification by reverse phase chromatography eluting with a 0.1% aqueous HCl/methanol gradient provided compound 7·2HCl as a yellow solid. MS (m/z) M+H=517.1

Synthesis of Compound 6

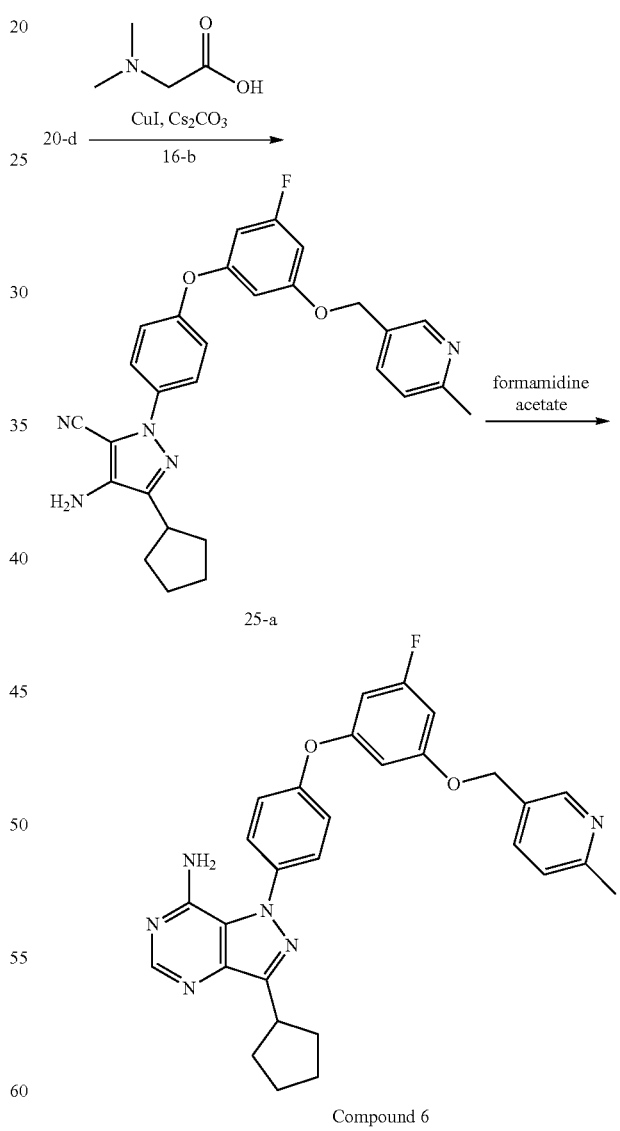

Step 1: Intermediate 25-a

To a solution of intermediate 20-d (200 mg, 0.74 mmol) in 1,4-dioxane (1.0 ml) was added intermediate 16-b (221 mg, 0.74 mmol), N,N-dimethylglycine (231 mg, 3.23 mmol), copper (I) iodide (142 mg, 0.74 mmol) and cesium carbonate (971 mg, 2.98 mmol). The reaction was heated in a sealed tube at 110° C. overnight and then cooled to room temperature, diluted with ethyl acetate and filtered over celite. Volatiles were removed under reduced pressure. Purification by silica gel chromatography provided intermediate 25-a as beige foam.

Step 2: Compound 6

To a solution of intermediate 25-a (360 mg, 0.74 mmol) in ethanol (7.45 ml) was added formamidine acetate (620 mg, 5.96 mmol) and the reaction was stirred at 80° C. for 3 hours and then cooled to room temperature. Volatiles were removed under reduced pressure. Purification by reverse phase chromatography eluting with a 0.1% aqueous HCl/methanol gradient provided compound 6·2HCl as a yellow solid. MS (m/z) M+H=511.2

Synthesis of Compound 8

Step 1: Intermediate 26-a

To a solution of intermediate 20-d (542 mg, 2.02 mmol) in 1,4-dioxane (2.70 ml) was added intermediate 17-b (600 mg, 2.02 mmol), N,N-dimethylglycine (416 mg, 4.04 mmol), copper (I) iodide (254 mg, 1.33 mmol) and cesium carbonate (1.97 g, 6.06 mmol). The reaction was heated in a sealed tube at 110° C. overnight and then cooled to room temperature, diluted with ethyl acetate and filtered over celite. Volatiles were removed under reduced pressure. Purification by silica gel chromatography provided intermediate 26-a as a beige foam.

Step 2: Compound 8

To a solution of intermediate 26-a (420 mg, 0.86 mmol) in ethanol (8.6 ml) was added formamidine acetate (722 mg, 6.93 mmol) and the reaction was stirred at 80° C. for 3 hours and then cooled to room temperature. Volatiles were removed under reduced pressure. Purification by reverse phase chromatography eluting with a 0.1% aqueous HCl/methanol gradient provided compound 8·2HCl as a yellow solid. MS (m/z) M+H=512.1

Synthesis of Compound 9

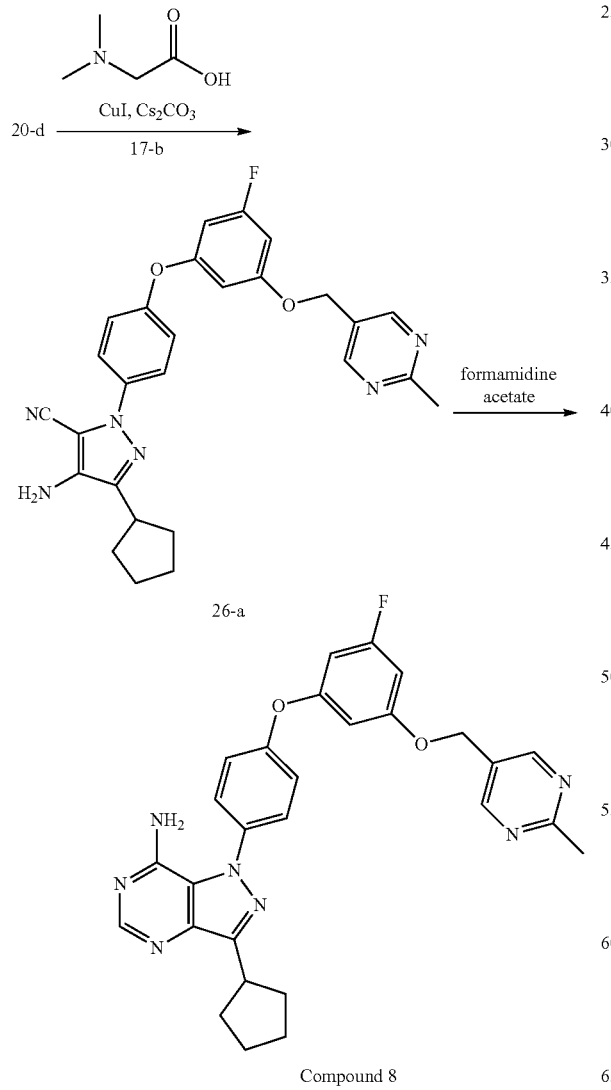

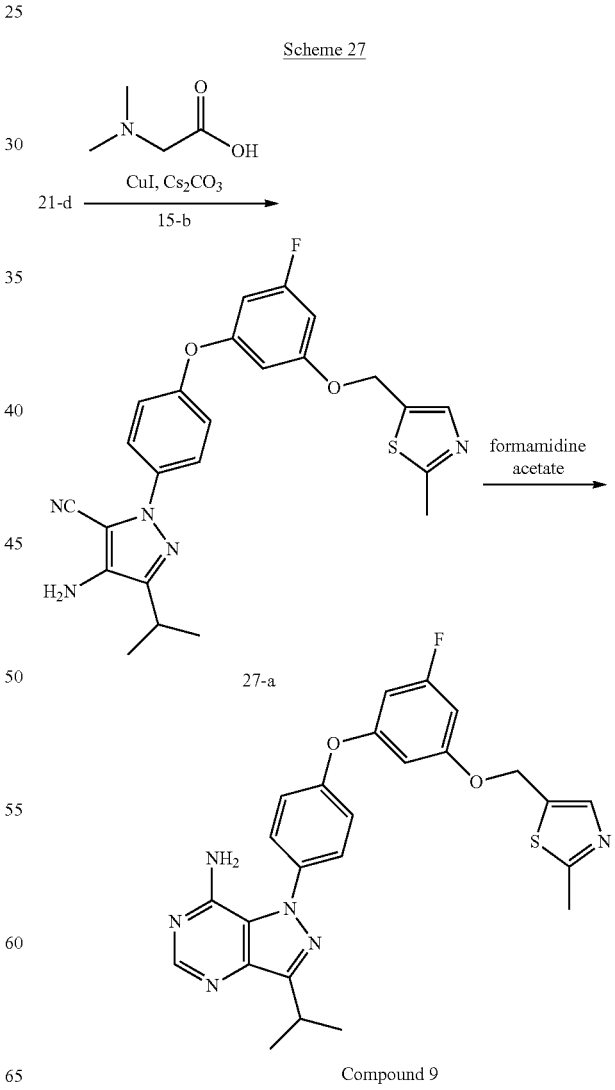

Step 1: Intermediate 27-a

To a solution of intermediate 21-d (2.30 g, 9.49 mmol) in 1,4-dioxane (12.7 ml) was added intermediate 15-b (2.87 g, 9.49 mmol), N,N-dimethylglycine (1.95 g, 19.0 mmol), copper (I) iodide (1.19 g, 6.27 mmol) and cesium carbonate (12.37 g, 38.0 mmol). The reaction was heated in a sealed tube at 110° C. overnight and then cooled to room temperature, diluted with ethyl acetate and filtered over celite. Volatiles were removed under reduced pressure. Purification by silica gel chromatography provided intermediate 27-a as a beige oil.

Step 2: Compound 9

To a solution of intermediate 27-a (1.65 g, 3.56 mmol) in ethanol (7.2 ml) was added formamidine acetate (741 mg, 6.93 mmol) and the reaction was stirred at 80° C. overnight and then cooled to room temperature. Water and ethyl acetate were added, the organic layer was separated, washed with brine, dried over $MgSO_4$, filtered and concentrated under reduced pressure. Volatiles were removed under reduced pressure. Purification by silica gel chromatography provided compound 9 as a white solid. Compound 9 was dissolved in methanol, the solution was acidified with 1N HCl in MeOH, a precipitated formed and was collected by filtration to provide compound 9·2HCl as a white solid. MS (m/z) M+H=491.1

Synthesis of Compound 11

Scheme 28

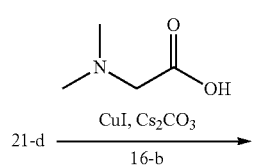

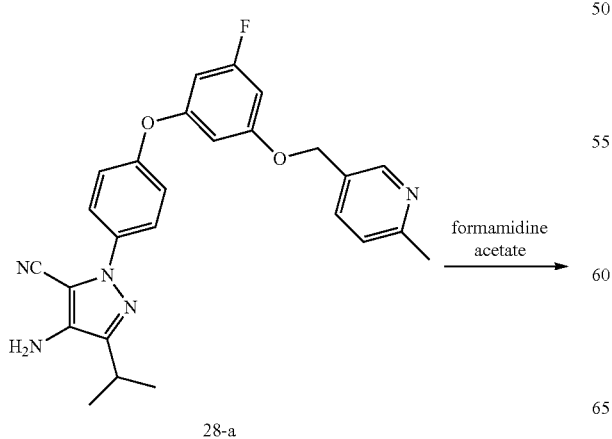

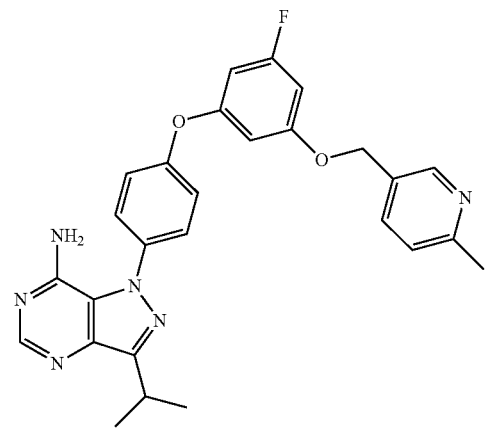

Compound 11

Step 1: Intermediate 28-a

To a solution of intermediate 21-d (491 mg, 2.03 mmol) in 1,4-dioxane (2.7 ml) was added intermediate 16-b (600 mg, 2.03 mmol), N,N-dimethylglycine (418 mg, 4.05 mmol), copper (I) iodide (255 mg, 1.33 mmol) and cesium carbonate (2.64 g, 8.10 mmol). The reaction was heated in a sealed tube at 110° C. overnight and then cooled to room temperature, diluted with ethyl acetate and filtered over celite. Volatiles were removed under reduced pressure. Purification by silica gel chromatography provided intermediate 28-a as a beige foam.

Step 2: Compound 11

To a solution of intermediate 28-a (510 mg, 1.11 mmol) in methanol (11.1 ml) was added formamidine acetate (1.16 g, 11.15 mmol), the reaction was stirred at reflux overnight and volatiles were removed under reduced pressure. Purification by reverse phase chromatography eluting with a 0.1% aqueous HCl/methanol gradient provided compound 11·2HCl as a white solid. MS (m/z) M+H=485.2

Synthesis of Compound 10

Scheme 29

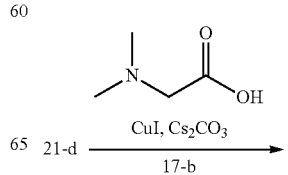

43

-continued

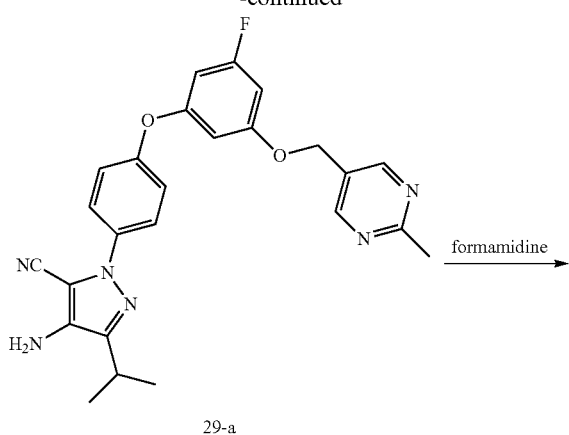

29-a

↓ formamidine

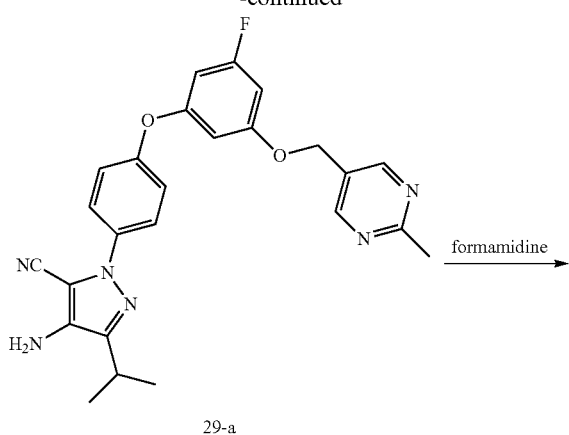

Compound 10

Step 1: Intermediate 29-a

To a solution of intermediate 21-d (2.0 g, 8.26 mmol) in 1,4-dioxane (11.0 ml) was added intermediate 17-b (2.45 g, 8.26 mmol), N,N-dimethylglycine (1.7 g, 16.5 mmol), copper (I) iodide (1.0 g, 5.45 mmol) and cesium carbonate (10.76 g, 33.0 mmol). The reaction was heated in a sealed tube at 110° C. overnight and then cooled to room temperature, diluted with ethyl acetate and filtered over celite. Volatiles were removed under reduced pressure. Purification by silica gel chromatography provided intermediate 29-a as a beige foam.

Step 2: Compound 10

To a solution of intermediate 29-a (1.5 g, 3.27 mmol) in methanol (32.7 ml) was added formamidine acetate (3.41 g, 32.7 mmol) and the reaction was stirred at reflux overnight and then cooled to room temperature. Water and ethyl acetate were added, the organic layer was separated, washed with brine, dried over $MgSO_4$, filtered and concentrated under reduced pressure. Volatiles were removed under reduced pressure. Methanol was added to the residue; a precipitated formed and was collected by filtration to provide compound 10 as a white solid. MS (m/z) M+H=486.2

44

Synthesis of Intermediate 30-a

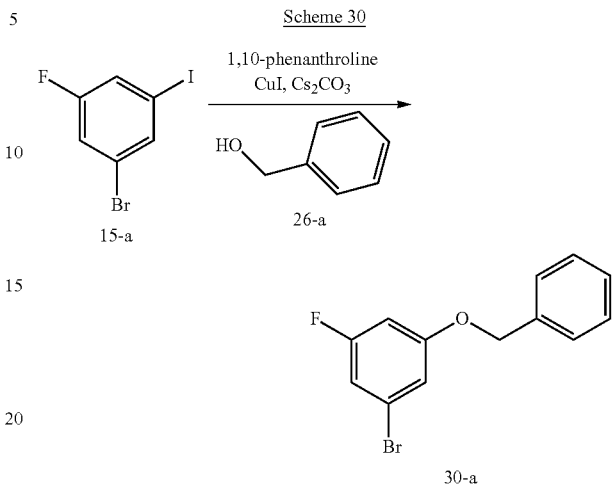

To a solution of 1-bromo-3-fluoro-5-iodobenzene 15-a (5.0 g, 16.62 mmol) in 1,4-dioxane (8.3 ml) was added benzyl alcohol 30-a (1.79 g, 16.62 mmol), 1,10-phenanthroline (599 mg, 3.32 mmol), copper (I) iodide (316 mg, 1.66 mmol) and cesium carbonate (7.58 g, 23.26 mmol). The reaction was stirred at 110° C. for 2 days and then cooled to room temperature, diluted with ethyl acetate and filtered over celite. A saturated aqueous solution of ammonium chloride was added to the filtrate, the organic layer was separated, and the aqueous phase was extracted twice with ethyl acetate. The combined organic extracts were washed with brine, dried over $MgSO_4$, filtered and concentrated under reduced pressure. Purification by silica gel chromatography provided intermediate 30-a as a beige oil.

Synthesis of Compound 12

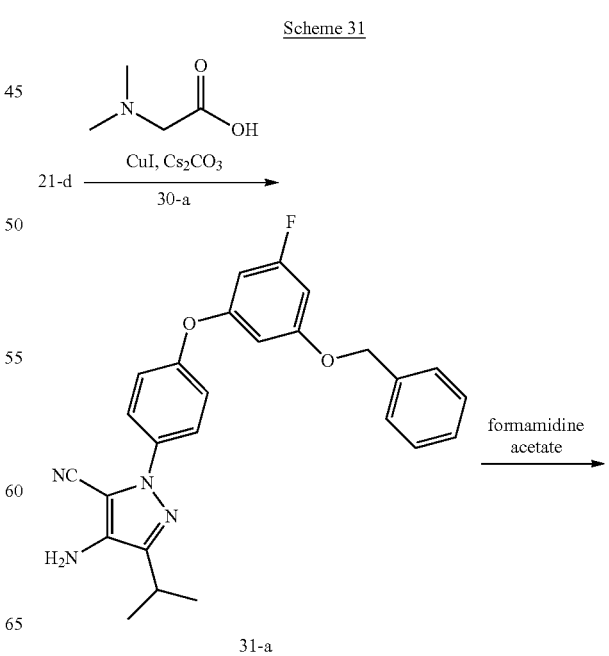

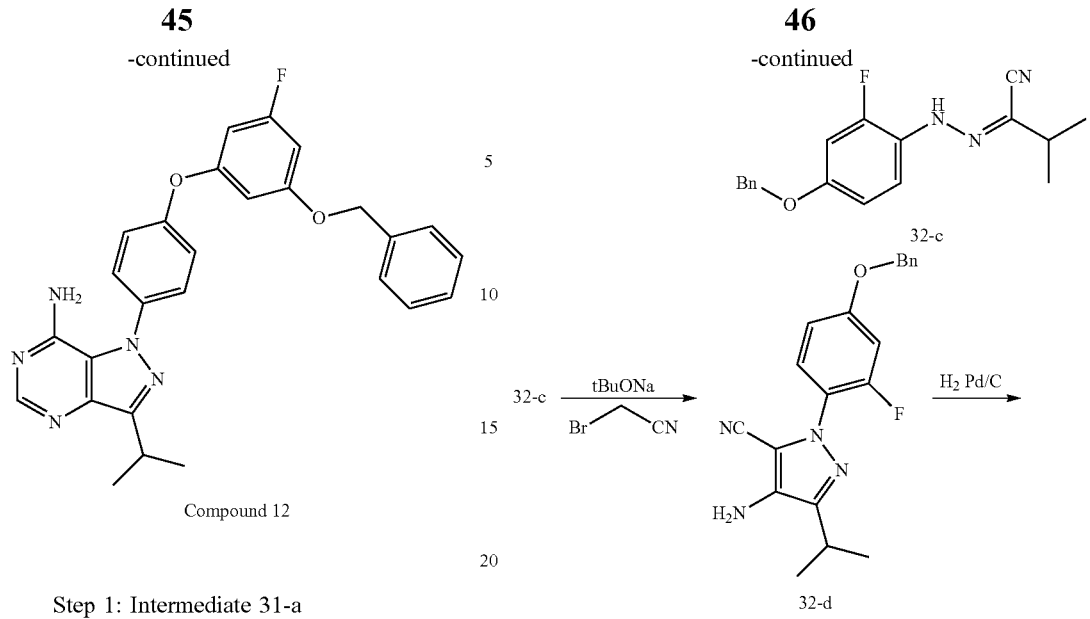

Compound 12

Step 1: Intermediate 31-a

To a solution of intermediate 21-d (370 mg, 1.52 mmol) in 1,4-dioxane (11.0 ml) was added intermediate 30-a (429 mg, 1.52 mmol), N,N-dimethylglycine (315 mg, 3.05 mmol), copper (I) iodide (192 mg, 1.0 mmol) and cesium carbonate (1.99 g, 6.11 mmol). The reaction was heated in a sealed tube at 110° C. overnight and then cooled to room temperature, diluted with ethyl acetate and filtered over celite. Volatiles were removed under reduced pressure. Purification by silica gel chromatography provided intermediate 31-a as a beige foam.

Step 2: Compound 12

To a solution of intermediate 31-a (130 mg, 0.29 mmol) in methanol (0.5 ml) was added formamidine acetate (306 mg, 2.94 mmol) and the reaction was stirred at reflux overnight and then cooled to room temperature. Volatiles were removed under reduced pressure. Purification by reverse phase chromatography eluting with a 0.1% aqueous HCl/methanol gradient provided compound 12.HCl as a yellow solid. MS (m/z) M+H=470.1

Synthesis of Intermediate 32-e

Scheme 32

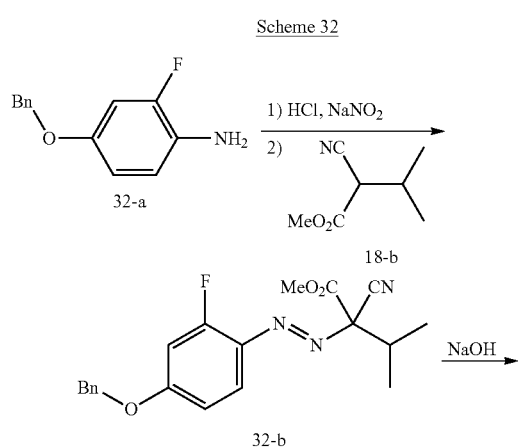

Step 1: Intermediate 32-b

To a solution of 4-(benzyloxy)-2-fluoroaniline 32-a (12.0 g, 47.3 mmol) in 1N HCl (39.9 ml) was added dropwise a 1.0 M solution of sodium nitrite (55.2 ml, 55.2 mmol) in water at room temperature, the mixture was stirred for 1 hour, filtered and then added dropwise to an ice cooled solution of intermediate 18-b (5.56 g, 39.4 mmol) in ethanol (10.6 ml) and water (146.0 mL). The PH was maintained at 7 by adding sodium acetate portion wise. The mixture was stirred at 0° C. for 3 hours and room temperature overnight. A saturated aqueous solution of ammonium chloride and ethyl acetate were added, the organic layer was separated, washed with brine, dried over MgSO₄, filtered and concentrated under reduced pressure to provide intermediate 32-b as a beige oil.

Step 2: Intermediate 32-c

To a solution of intermediate 32-b (15.0 g, 40.6 mmol) in a 1:1 mixture of 1,4-dioxane/water (203.0 ml) cooled to 0° C. was added NaOH 10N (81.0 ml, 812.0 mmol) and the reaction was stirred at room temperature for 1 hour. A saturated aqueous solution of ammonium chloride and ethyl acetate were added, the organic layer was separated, washed with brine, dried over MgSO₄, filtered and concentrated under reduced pressure to provide intermediate 32-c as a beige oil.

Step 3: Intermediate 32-d

To a solution of intermediate 32-c (5.5 g, 17.6 mmol) in tBuOH (80 ml) at room temperature, was added a 1.0 M solution of tBuOK in tBuOH (37.1 ml, 37.1 mmol). The reaction was stirred for 15 minutes at room temperature and bromoacetonitrile (3.08 ml, 44.2 mmol) was added dropwise. After the addition was completed the reaction was stirred for an additional 3 hours. A saturated aqueous solution of ammonium chloride and ethyl acetate were added, the organic layer was separated and the organic phase was extracted twice with ethyl acetate. The combined organic extracts were washed with brine, dried over MgSO$_4$ filtered and concentrated under reduced pressure. Purification by silica gel chromatography provided intermediate 32-d as a beige oil.

Step 4: Intermediate 32-e

To a solution of intermediate 32-d (1.0 g, 14.3 mmol) in ethyl acetate and stirred under nitrogen was added 10% Pd/C (607 mg, 0.3 mmol). The reaction mixture was purged with H$_2$ and stirred for 3 hours under 1 atm of hydrogen. The reaction was then filtered through celite and the filtrate was concentrated in vacuo. Purification by silica gel chromatography provided intermediate 32-e as a yellow solid.

Synthesis of Compound 16

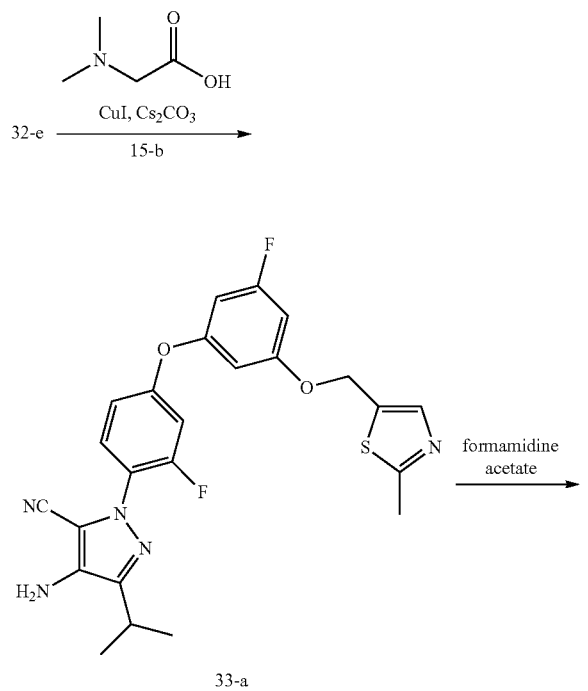

Scheme 33

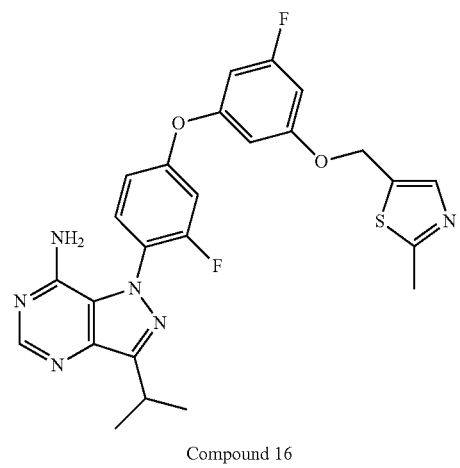

Compound 16

Step 1: Intermediate 33-a

To a solution of intermediate 32-e (200 mg, 0.7 mmol) in 1,4-dioxane (1.0 ml) was added intermediate 15-b (255 mg, 0.8 mmol), N,N-dimethylglycine (158 mg, 1.5 mmol), copper (I) iodide (97 mg, 0.5 mmol) and cesium carbonate (1.0 g, 3.1 mmol). The reaction was heated in a sealed tube at 110° C. for 2 days and then cooled to room temperature, diluted with ethyl acetate and filtered over celite. Volatiles were removed under reduced pressure. Purification by silica gel chromatography provided intermediate 33-a as a beige foam.

Step 2: Compound 16

To a solution of intermediate 33-a (70 mg, 0.1 mmol) in isopropanol (10.0 ml) was added formamidine acetate (151 mg, 1.4 mmol) and the reaction was stirred at 100° C. overnight and then cooled to room temperature. Volatiles were removed under reduced pressure. Purification by reverse phase chromatography eluting with a 0.1% aqueous HCl/methanol gradient provided compound 16·2HCl as a yellow solid. MS (m/z) M+H=509.1

Synthesis of Compound 17

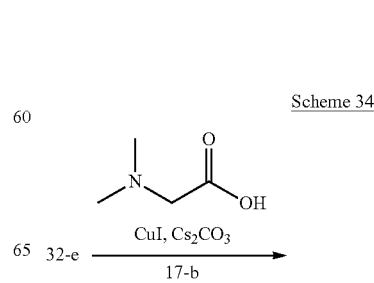

Scheme 34

-continued

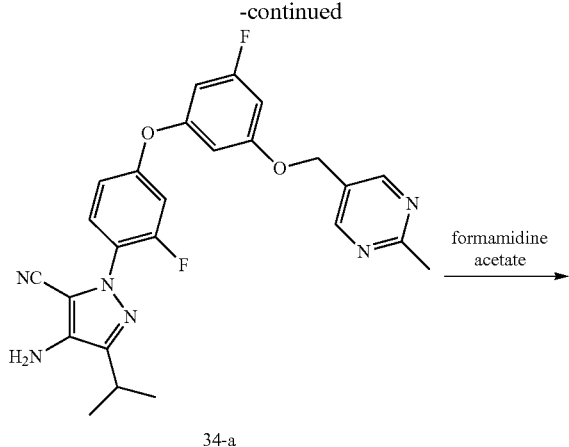

34-a

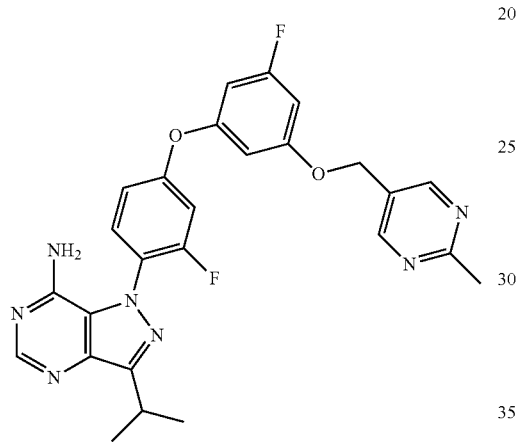

Compound 17

Step 1: Intermediate 34-a

To a solution of intermediate 32-e (200 mg, 0.7 mmol) in 1,4-dioxane (1.0 ml) was added intermediate 17-b (251 mg, 0.8 mmol), N,N-dimethylglycine (158 mg, 1.5 mmol), copper (I) iodide (97 mg, 0.5 mmol) and cesium carbonate (1.0 g, 3.1 mmol). The reaction was heated in a sealed tube at 110° C. for 2 days and then cooled to room temperature, diluted with ethyl acetate and filtered over celite. Volatiles were removed under reduced pressure. Purification by silica gel chromatography provided intermediate 34-a as a beige foam.

Step 2: Compound 17

To a solution of intermediate 34-a (35 mg, 0.07 mmol) in isopropanol (10.0 ml ml) was added formamidine acetate (76 mg, 0.7 mmol) and the reaction was stirred at reflux overnight and then cooled to room temperature. Volatiles were removed under reduced pressure. Purification by reverse phase chromatography eluting with a 0.1% aqueous HCl/methanol gradient provided compound 17·2HCl as a yellow solid. MS (m/z) M+H=504.1

TABLE 1

Example Compounds of Formula 1

| Com-pound | Structure | MS (m/z) |
|---|---|---|
| 1 | 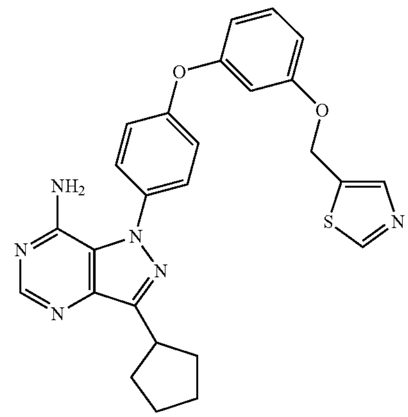 [SMILES: Nc1ncnc2c(C3CCCC3)nn(-c3ccc(Oc4cccc(OCc5cncs5)c4)cc3)c12] | $[M + H]^+ = 485.2$ |
| 2 | 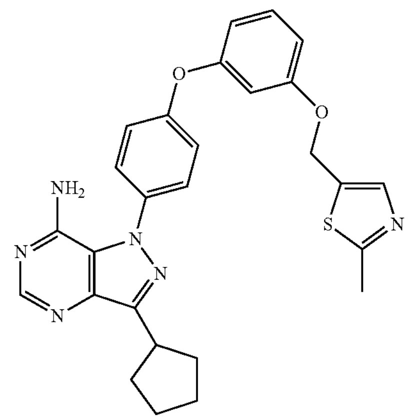 [SMILES: Cc1ncc(COc2cccc(Oc3ccc(-n4nc(C5CCCC5)c5ncnc(N)c54)cc3)c2)s1] | $[M + H]^+ = 499.2$ |
| 3 | 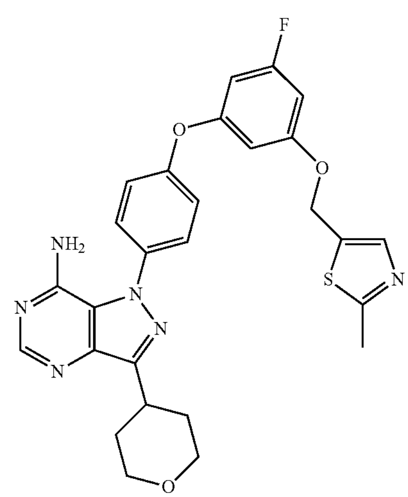 [SMILES: Cc1ncc(COc2cc(F)cc(Oc3ccc(-n4nc(C5CCOCC5)c5ncnc(N)c54)cc3)c2)s1] | $[M + H]^+ = 533.1$ |

TABLE 1-continued

Example Compounds of Formula 1

| Compound | Structure | MS (m/z) |
|---|---|---|
| 4 | 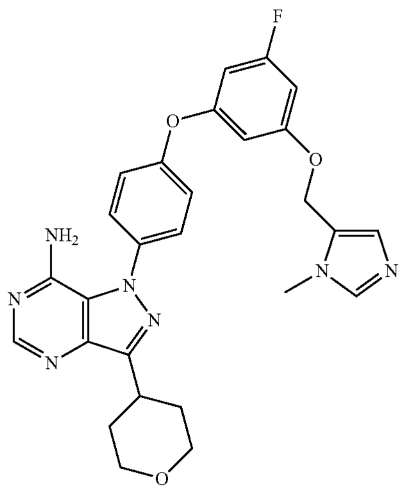 [SMILES: Cn1cncc1COc1cc(F)cc(Oc2ccc(-n3nc(C4CCOCC4)c4ncnc(N)c43)cc2)c1] | [M + H]⁺ = 516.2 |
| 5 | 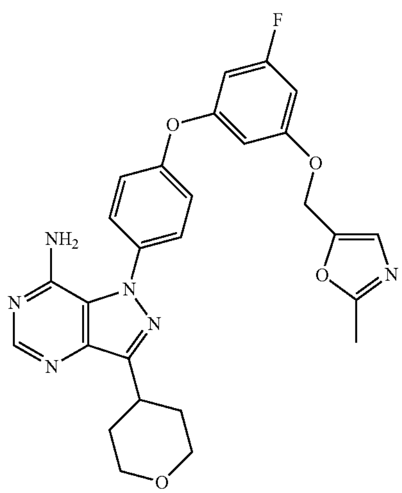 [SMILES: Cc1ncc(COc2cc(F)cc(Oc3ccc(-n4nc(C5CCOCC5)c5ncnc(N)c54)cc3)c2)o1] | [M + H]⁺ = 517.2 |
| 6 | 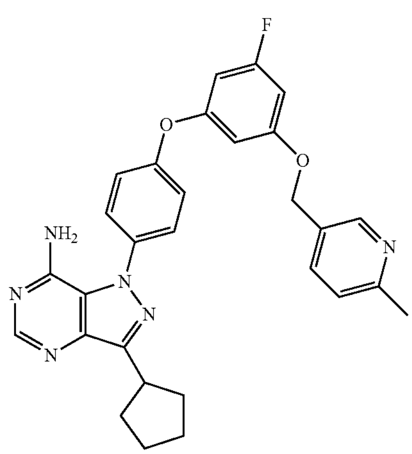 [SMILES: Cc1ccc(COc2cc(F)cc(Oc3ccc(-n4nc(C5CCCC5)c5ncnc(N)c54)cc3)c2)cn1] | [M + H]⁺ = 511.2 |
| 7 | | [M + H]⁺ = 517.2 |
| 8 | | [M + H]⁺ = 512.1 |
| 9 | | [M + H]⁺ = 491.1 |

TABLE 1-continued

Example Compounds of Formula 1

| Compound | Structure | MS (m/z) |
|---|---|---|
| 10 | 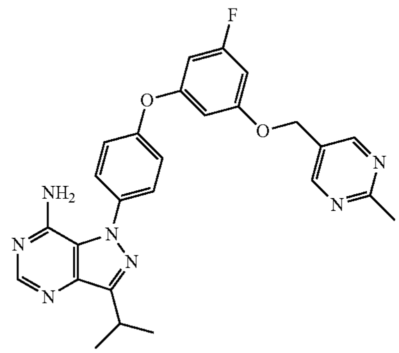 [SMILES: Cc1ncc(COc2cc(F)cc(Oc3ccc(-n4nc(C(C)C)c5ncnc(N)c54)cc3)c2)cn1] | [M + H]⁺ = 486.2 |
| 11 | 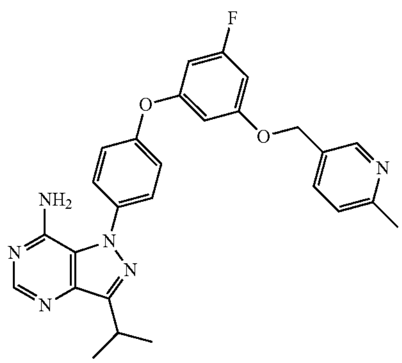 [SMILES: Cc1ccc(COc2cc(F)cc(Oc3ccc(-n4nc(C(C)C)c5ncnc(N)c54)cc3)c2)cn1] | [M + H]⁺ = 485.2 |
| 12 | 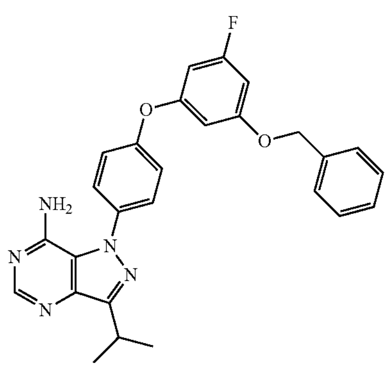 [SMILES: CC(C)c1nn(-c2ccc(Oc3cc(F)cc(OCc4ccccc4)c3)cc2)c2c(N)ncnc12] | [M + H]⁺ = 470.1 |
| 13 | 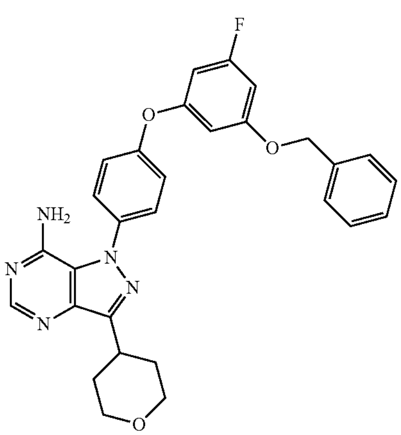 [SMILES: Nc1ncnc2c(C3CCOCC3)nn(-c3ccc(Oc4cc(F)cc(OCc5ccccc5)c4)cc3)c12] | [M + H]⁺ = 512.1 |
| 14 | | [M + H]⁺ = 527.2 |
| 15 | | [M + H]⁺ = 528.1 |
| 16 | | [M + H]⁺ = 509.1 |

TABLE 1-continued

Example Compounds of Formula 1

| Compound | Structure | MS (m/z) |
|---|---|---|
| 17 | 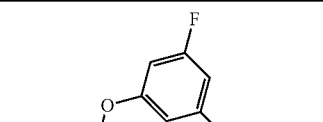 | $[M + H]^+ =$ 504.1 |

Kinase Binding

Btk Kinase Inhibition Assay

Fluorescence polarization-based kinase assays were performed in 384 well-plate format using histidine tagged recombinant human full-length Bruton Agammaglobulinemia Tyrosine Kinase (Btk) and a modified protocol of the KinEASE™ FP Fluorescein Green Assay supplied from Millipore. Kinase reaction were performed at room temperature for 60 minutes in presence of 250 µM substrate, 10 µM ATP and variable test article concentrations. The reaction was stopped with EDTA/kinease detection reagents and the polarization measured on a Tecan 500 instrument. From the dose-response curve obtained, the $IC_{50}$ was calculated using Graph Pad Prisms® using a non linear fit curve. The Km for ATP on each enzyme was experimentally determined and the Ki values calculated using the Cheng-Prusoff equation (see: Cheng Y, Prusoff W H. (1973) Relationship between the inhibition constant (K1) and the concentration of inhibitor which causes 50 percent inhibition ($I_{50}$) of an enzymatic reaction". *Biochem Pharmacol* 22 (23): 3099-108).

$k_i$ values are reported in Table 2:

TABLE 2

Inhibition of Btk

| Compound | $k_i$ (nM) |
|---|---|
| 1 | a |
| 2 | a |
| 3 | a |
| 4 | a |
| 5 | a |
| 6 | a |
| 7 | a |
| 8 | a |
| 9 | a |
| 10 | a |
| 11 | a |
| 12 | a |
| 13 | a |
| 14 | a |
| 15 | a |
| 16 | — |
| 17 | — | a - Ki < 100 nM;
b - 100 nM < Ki < 1000 nM,
c - ki > 1000 nM

Splenic Cell Proliferation Assay

Splenocytes were obtained from 6 week old male CD1 mice (Charles River Laboratories Inc.). Mouse spleens were manually disrupted in PBS and filtered using a 70 um cell strainer followed by ammonium chloride red blood cell lysis. Cells were washed, resuspended in Splenocyte Medium (HyClone RPMI supplemented with 10% heat-inactivated FBS, 0.5× non-essential amino acids, 10 mM HEPES, 50 uM beta mercaptoethanol) and incubated at 37° C., 5% $CO_2$ for 2 h to remove adherent cells. Suspension cells were seeded in 96 well plates at 50,000 cells per well and incubated at 37° C., 5% $CO_2$ for 1 h. Splenocytes were pre-treated in triplicate with 10,000 nM curves of Formula 1 compounds for 1 h, followed by stimulation of B cell proliferation with 2.5 ug/ml anti-IgM F(ab')$_2$ (Jackson ImmunoResearch) for 72 h. Cell proliferation was measured by Cell Titer-Glo Luminescent Assay (Promega). $EC_{50}$ values (50% proliferation in the presence of compound as compared to vehicle treated controls) were calculated from dose response compound curves using GraphPad Prism Software.

$EC_{50}$ values are reported in Table 3:

TABLE 3

Inhibition of splenic cell proliferation

| Compound | $EC_{50}$ (nM) |
|---|---|
| 1 | a |
| 2 | a |
| 3 | a |
| 4 | a |
| 5 | a |
| 6 | a |
| 7 | a |
| 8 | a |
| 9 | a |
| 10 | a |
| 11 | a |
| 12 | a |
| 13 | a |
| 14 | a |
| 15 | — |
| 16 | — |
| 17 | — | a - $EC_{50}$ < 100 nM;
b - 100 nM < $EC_{50}$ < 1000 nM,
c - $EC_{50}$ > 1000 nM

Methods: Mouse Arthus

Mouse Arthus studies were conducted as reported in Braselmann S, Taylor V, Zhao H, Wang S, Sylvain C, Baluom M, Qu K, Herlaar E, Lau A, Young C, Wong B R, Lovell S, Sun T, Park G, Argade A, Jurcevic S, Pine P, Singh R, Grossbard E B, Payan D G, Masuda E S: R406 an orally available spleen tyrosine kinase inhibitor blocks fc receptor signaling and reduces immune-complex mediated inflammation. *J Pharmacol Exp Ther*, 2006, 319:998-1008.

In summary, female Balb/c mice (6-7 weeks on arrival) were habituated to the animal facility for at least 4 days. On the day of the experiment, animals were pre-treated (t=minus 1 h) with compound or vehicle alone by gavage (PO). At t=0, animals were injected intravenously (IV; 0.1 mL/mouse) with saline containing chicken ovalbumin and Evan's blue (10 mg/mL of each). Ten minutes later (t=10 min), animals were anesthesized with isoflurane, the dorsal surface was shaved and rabbit anti-chicken ovalbumin antibody was then injected intradermally at one site on the right side of the animal (25 μg in 30 μL). The same amount of isotype control antibody was then injected on the left side.

The animals were then returned to their home cage and skin punches (8 mm) were collected from each injection site four hours later. The samples were placed in 1 mL formamide overnight at 80 degrees C. (1 skin biopsy per 1 mL formamide in a glass tube). The amount of Evan's blue in the formamide solution was then assessed by spectrophotometry (630 nm) as a measure of serum extravasation into the dermis.

Compounds 9 and 10 demonstrated efficacy when delivered orally at 30 mg/kg.

The invention claimed is:

1. A compound of Formula 1:

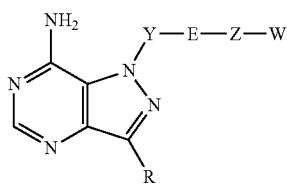

Formula 1 wherein
R is selected from the group consisting of:
  1) hydrogen,
  2) alkyl,
  3) heteroalkyl,
  4) carbocyclyl,
  5) heterocyclyl,
wherein the alkyl, heteroalkyl, carbocyclyl and heterocyclyl may be further substituted;
Y is

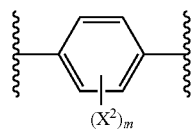

E is oxygen,
Z is

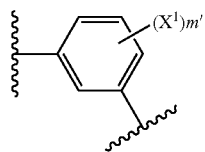

wherein Y-E-Z-W is

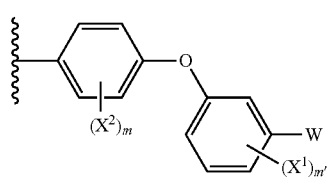

$X^1$ and $X^2$ are independently selected from hydrogen and halogen;

n is an integer from 0 to 2;
m is an integer from 0 to 2;
m' is an integer from 0 to 2;
W is selected from the group consisting of:
  1) halogen,
  2) aralkyl,
  3) heteroaralkyl,
  4) —$OR^3$,
  5) —$OC(O)R^4$,
  6) —$OC(O)NR^5R^6$,
  7) —$CH_2O$—$R^4$,
  8) —$NR^5R^6$
  9) —$NR^2C(O)R^4$,
  10) —$NR^2S(O)_nR^4$,
  11) —$NR^2C(O)NR^5R^6$,
wherein the aralkyl and heteraralkyl may be further substituted;
$R^2$ is selected from the group consisting of hydrogen and alkyl;
$R^3$ is selected from the group consisting of substituted alkyl, unsubstituted alkyl, alkenyl, alkynyl, heteroalkyl, carbocyclyl, heterocyclyl, aryl, heteroaryl, aralkyl, and heteroaralkyl;
$R^4$ is selected from the group consisting of substituted alkyl, unsubstituted alkyl, alkenyl, alkynyl, heteroalkyl, carbocyclyl, heterocyclyl, aryl, and heteroaryl; and
$R^5$ and $R^6$ are (i) independently selected from the group consisting of hydrogen, alkyl, alkenyl, alkynyl, heteroalkyl, carbocyclyl, heterocyclyl, aryl, and heteroaryl; or
(ii) fused to form a 3 to 8 membered heterocyclyl ring system; or
a pharmaceutically acceptable salt, solvate or solvate of a salt thereof.

2. The compound according to claim 1, wherein W is —OR' and $R^3$ is selected from the group consisting of substituted aralkyl, unsubstituted aralkyl, substituted heteroaralkyl and/or unsubstituted heteroaralkyl.

3. The compound according to claim 1, wherein R is selected from the group consisting of:

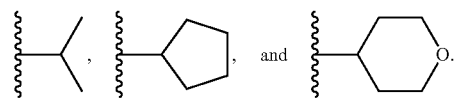

4. The compound according to claim 1, wherein Z is selected from the group consisting of:

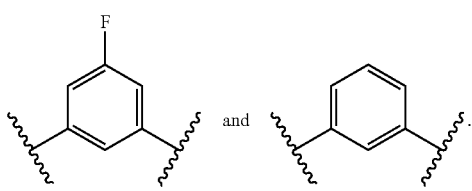 [SMILES: *c1cc(*)cc(F)c1 ; *c1cccc(*)c1]

5. The compound according to claim 2, wherein W is selected from the group consisting of:

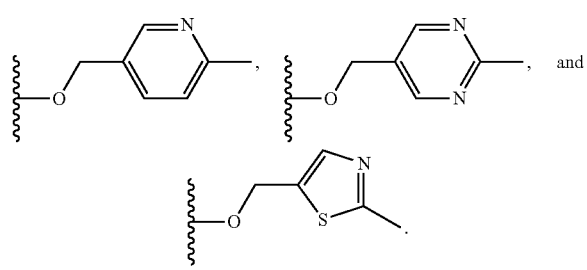
6. The compound according to claim 1 selected from the group consisting of:
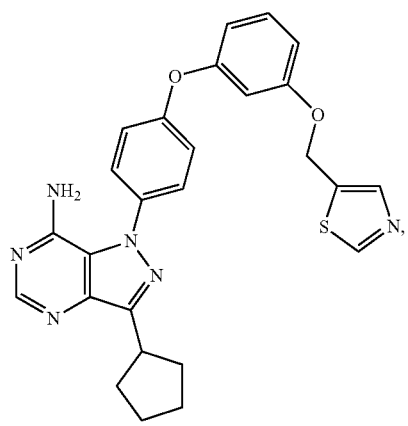
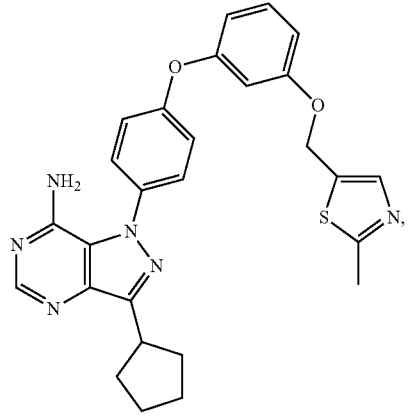
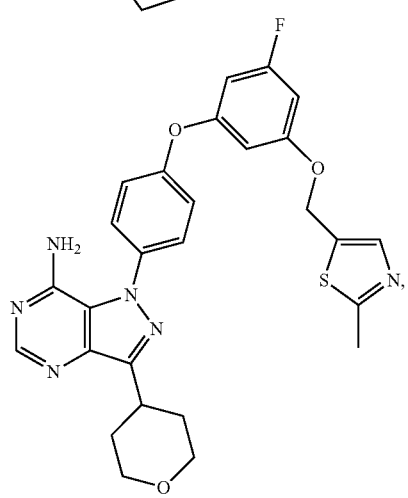
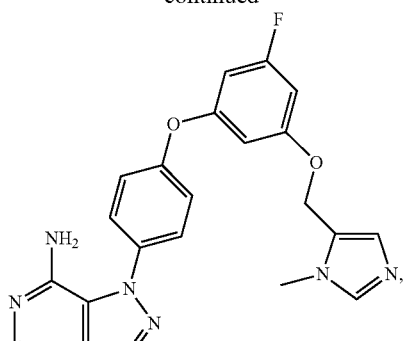
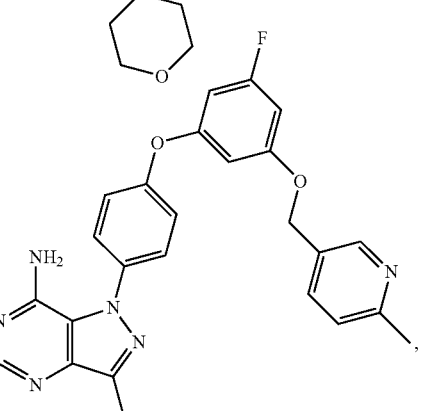
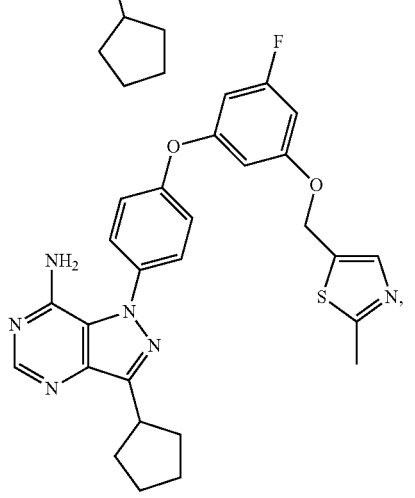

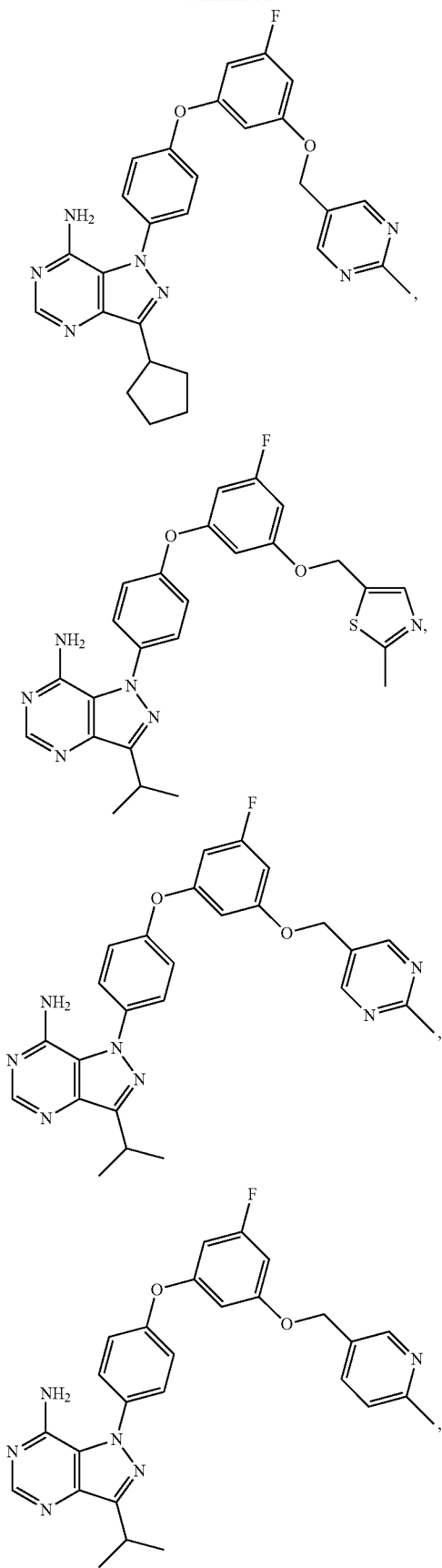
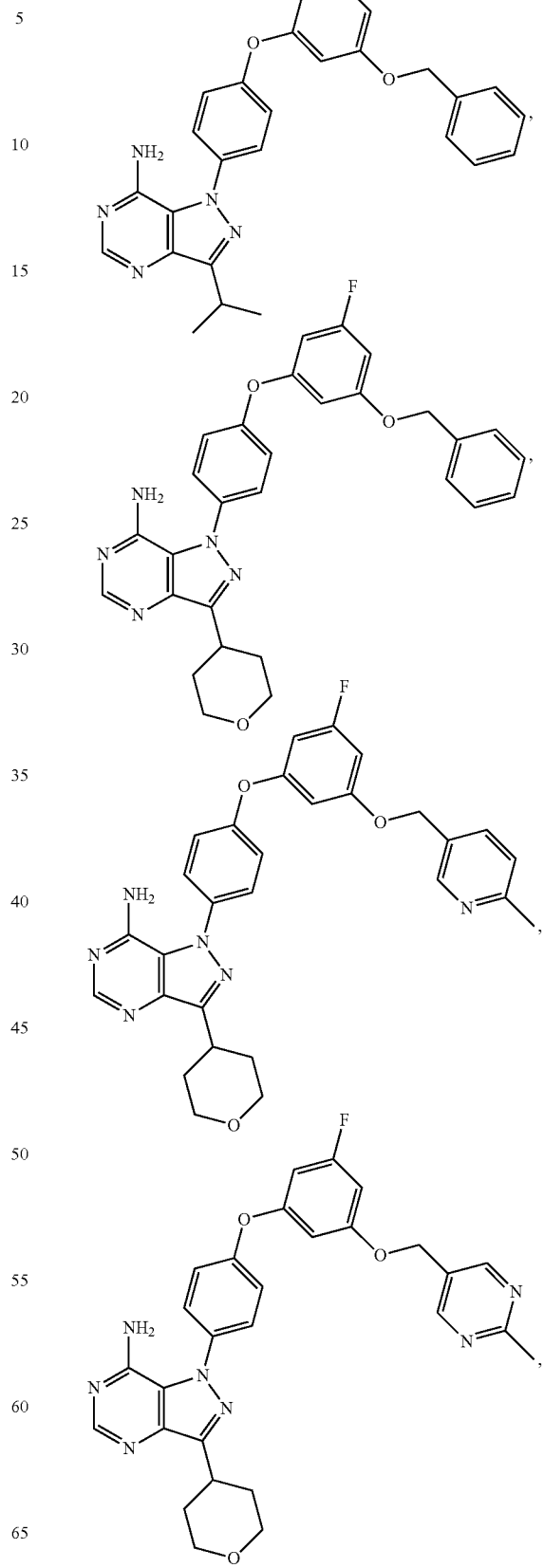

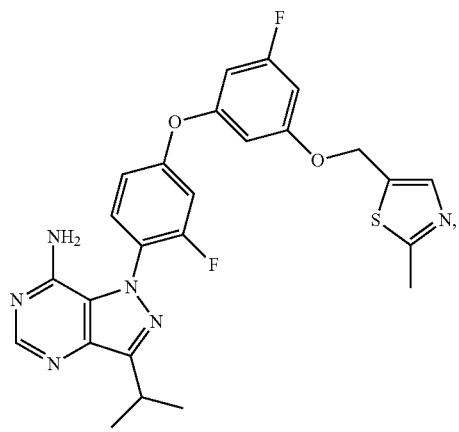
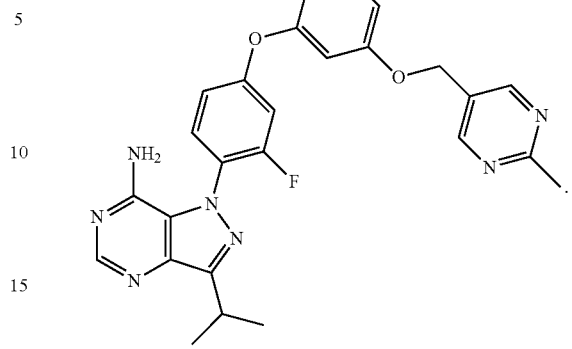
7. A pharmaceutical composition comprising a compound of claim 1, or a pharmaceutically acceptable salt, or solvate thereof, and at least one pharmaceutically acceptable excipient.
* * * * *